(12) United States Patent
Stephens

(10) Patent No.: US 11,670,129 B2
(45) Date of Patent: Jun. 6, 2023

(54) MEDICATION MANAGEMENT SYSTEMS AND METHODS FOR HEALTH AND HEALTH-RELATED FACILITIES

(71) Applicant: BTP Fund, LP, Austin, TX (US)

(72) Inventor: Stewart W. Stephens, Murphy, TX (US)

(73) Assignee: BTP Fund, LP, Austin, TX (US)

( * ) Notice: Subject to any disclaimer, the term of this patent is extended or adjusted under 35 U.S.C. 154(b) by 363 days.

(21) Appl. No.: 17/012,829

(22) Filed: Sep. 4, 2020

(65) Prior Publication Data

US 2020/0411156 A1 Dec. 31, 2020

Related U.S. Application Data

(63) Continuation of application No. 16/259,716, filed on Jan. 28, 2019, now Pat. No. 11,217,058, which is a (Continued)

(51) Int. Cl.
*G16H 10/60* (2018.01)
*G07F 17/00* (2006.01)
(Continued)

(52) U.S. Cl.
CPC ......... *G07F 17/0092* (2013.01); *G06Q 50/22* (2013.01); *G07F 9/001* (2020.05);
(Continued)

(58) Field of Classification Search
USPC ....................................................... 705/2–3
See application file for complete search history.

(56) References Cited

U.S. PATENT DOCUMENTS 4,695,954 A 9/1987 Rose
5,502,944 A * 4/1996 Kraft .................. G07F 17/0092
700/242
(Continued)

FOREIGN PATENT DOCUMENTS

CA 2830358 10/2011
WO WO-2010/022506 3/2010
WO WO-201/1130296 10/2011

OTHER PUBLICATIONS

U.S. Appl. No. 16/259,716, Non-Final Office Action dated Nov. 9, 2020, 16 pgs.
(Continued)

*Primary Examiner* — Michael Tomaszewski
(74) *Attorney, Agent, or Firm* — Foley & Lardner LLP

(57) ABSTRACT

A system and method for control of prescription drug packaging and dispensing machines located in an in-patient health care facility including centralized control and enhanced communication between system components. Delay and errors in processing item data in the prescription dispensing system are reduced by using concise ID data incorporated into each canister memory chip and storing canister contents data elsewhere. Canisters are configured in a pharmacy using interchangeable parts. Data being processed is synchronized by a combination of user tokens (who), data identifiers (what), and unique Ids for the entities in the system (where). The foregoing combination enables substantial efficiency improvements and error reduction.

28 Claims, 16 Drawing Sheets

Related U.S. Application Data continuation of application No. 15/050,460, filed on Feb. 22, 2016, now Pat. No. 10,192,035, which is a continuation of application No. 13/085,298, filed on Apr. 12, 2011, now Pat. No. 9,268,912.

(60) Provisional application No. 61/323,125, filed on Apr. 12, 2010.

(51) Int. Cl.
*G07F 9/00* (2006.01)
*G06Q 50/22* (2018.01)
*G16H 20/13* (2018.01)

(52) U.S. Cl.
CPC .............. *G07F 9/002* (2020.05); *G16H 10/60* (2018.01); *G16H 20/13* (2018.01)

(56) References Cited

U.S. PATENT DOCUMENTS

| | | | |
|---|---|---|---|
| 5,597,995 A | | 1/1997 | Williams et al. |
| 5,771,657 A | | 6/1998 | Lasher et al. |
| 5,883,370 A | * | 3/1999 | Walker ............... G16H 20/10 235/462.15 |
| 6,006,946 A | * | 12/1999 | Williams ............ G16H 20/13 221/9 |
| 6,036,812 A | * | 3/2000 | Williams ............ G07F 11/62 414/226.02 |
| 6,176,392 B1 | * | 1/2001 | William ............... G07F 11/24 221/109 |
| 6,338,007 B1 | | 1/2002 | Broadfield et al. |
| 6,529,446 B1 | | 3/2003 | de la Huerga |
| 6,611,733 B1 | * | 8/2003 | De La Huerga ........................ G06K 19/07762 700/235 |
| 7,440,818 B2 | | 10/2008 | Handfield et al. |
| 7,469,213 B1 | | 12/2008 | Rao |
| 7,543,718 B2 | | 6/2009 | Simon |
| 7,698,019 B2 | | 4/2010 | Moncrief et al. |
| 7,706,915 B2 | | 4/2010 | Mohapatra et al. |
| 7,809,467 B2 | | 10/2010 | Schaefer |
| 7,810,726 B2 | | 10/2010 | de la Huerga |
| 8,065,035 B2 | | 11/2011 | Ross et al. |
| 8,195,328 B2 | | 6/2012 | Mallett et al. |
| 9,268,912 B2 | | 2/2016 | Stephens |
| 10,192,035 B2 | | 1/2019 | Stephens |
| 2002/0032582 A1 | | 3/2002 | Feeney et al. |
| 2002/0173875 A1 | | 11/2002 | Wallace et al. |
| 2002/0190075 A1 | | 12/2002 | Weldi et al. |
| 2003/0024943 A1 | * | 2/2003 | MacDonald ........ G07F 17/0092 221/92 |
| 2003/0050731 A1 | | 3/2003 | Rosenblum |
| 2003/0140929 A1 | | 7/2003 | Wilkes et al. |
| 2003/0187692 A1 | | 10/2003 | Park |
| 2004/0172281 A1 | | 9/2004 | Stanners |
| 2004/0193454 A1 | | 9/2004 | Foote et al. |
| 2004/0204954 A1 | | 10/2004 | Lacko |
| 2005/0131733 A1 | | 6/2005 | Bow |
| 2006/0025884 A1 | | 2/2006 | Henkel |
| 2006/0054682 A1 | | 3/2006 | de la Huerga |
| 2006/0058725 A1 | | 3/2006 | Handfield et al. |
| 2006/0200369 A1 | | 9/2006 | Batch et al. |
| 2006/0277269 A1 | | 12/2006 | Dent et al. |
| 2007/0043469 A1 | | 2/2007 | Draper |
| 2007/0156452 A1 | | 7/2007 | Batch |
| 2007/0214014 A1 | | 9/2007 | Suwalski et al. |
| 2007/0233520 A1 | | 10/2007 | Wehba et al. |
| 2008/0015897 A1 | | 1/2008 | Moradi et al. |
| 2008/0059228 A1 | | 3/2008 | Bossi et al. |
| 2008/0086333 A1 | | 4/2008 | Hertel et al. |
| 2008/0173711 A1 | | 7/2008 | Handfield et al. |
| 2008/0179387 A1 | | 7/2008 | Cantlay et al. |
| 2008/0316045 A1 | | 12/2008 | Sriharto et al. |
| 2008/0319790 A1 | | 12/2008 | Vahlberg et al. |
| 2009/0012820 A1 | | 1/2009 | Bishop et al. |
| 2009/0132083 A1 | | 5/2009 | Rice et al. |
| 2009/0164042 A1 | | 6/2009 | Handfield et al. |
| 2009/0182582 A1 | | 7/2009 | Hammon |
| 2009/0240528 A1 | | 9/2009 | Bluth |
| 2009/0299522 A1 | | 12/2009 | Savir et al. |
| 2009/0321469 A1 | | 12/2009 | Knoth |
| 2010/0017296 A1 | | 1/2010 | Spignesi, Jr. et al. |
| 2010/0030667 A1 | * | 2/2010 | Chudy ................ G06Q 10/08 705/28 |
| 2010/0071320 A1 | | 3/2010 | Ali et al. |
| 2010/0114367 A1 | | 5/2010 | Barrett et al. |
| 2011/0093279 A1 | * | 4/2011 | Levine ................ G06F 16/24 235/375 |
| 2011/0251850 A1 | | 10/2011 | Stephens |
| 2012/0083666 A1 | | 4/2012 | Waugh et al. |
| 2012/0124938 A1 | | 5/2012 | Yasunaga et al. |
| 2012/0173287 A1 | | 7/2012 | Cowand |
| 2013/0151003 A1 | | 6/2013 | Gillum |
| 2016/0171176 A1 | | 6/2016 | Stephens |

OTHER PUBLICATIONS

U.S. Appl. No. 16/259,716, Notice of Allowance dated Jun. 28, 2021, 9 pgs.
Australian Pat. Appl. No. 2018233018, Examination Report dated Oct. 15, 2020, 9 pgs.
U.S. Appl. No. 16/259,716, Final Office Action dated Mar. 4, 2021, 26 pgs.
European Search Report re EP 11769456.2 dated Aug. 21, 2018, 15 pages.
International Preliminary Report on Patentability, including the Written Opinion of the International Searching Authority for International Application No. PCT/US2011/032150, dated Oct. 16, 2012 (8 pgs.).
International Search Report for International Application No. PCT/US2011/032150, dated Jul. 5, 2011, (2 pgs.).
Supplementary European Search Report for EP11769456 dated Mar. 17, 2015.
U.S. Appl. No. 16/259,716, Non-Final Office Action dated Oct. 6, 2020, 16 pgs.

* cited by examiner

FIG. 1
*(PRIOR ART)*

| | 1 | 2 | 3 | 4 | 5 | 6 | 7 | 8 | 9 | 10 | 11 | 12 | 13 | 14 | 15 | 16 | 17 | 18 | 19 ~ 2027 | nByte+1 | nByte+4 | nByte+1 |
|---|---|---|---|---|---|---|---|---|---|---|---|---|---|---|---|---|---|---|---|---|---|---|
| | 1 | 1 | 2 | 3 | 1 | 2 | 3 | 4 | 5 | 6 | 7 | 8 | 9 | 10 | 11 | 12 | 13 | 14 | Free Space (2009byte) | | | |
| | | | | | | | | | | | | | | | | | 15 | Chip Memory Data | | | |
| SOC | Canister ID 18 | | | Chip ID 20 | | | | | | | | | | | | | | | Parity | Check Sum | EOC |
| 0x0A | 0x80 ~ 0xE3 | | | 0x20 ~ 0x7E (Exception 0x7C) | | | | | | | | | | | | | | 0x20 ~ 0xFF | 0x30 ~ 0x39 | 0x30 ~ 0x39 | 0x03 |

FIG. 2

| | 1 | 2 | 3 | 4 | 5 | 6 | 7 | 8 | 9 | 10 | 11 | 12 | 13 | 14 | 15 | 16 | 17 | 18 | nByte+1 | nByte+4 | nByte+1 |
|---|---|---|---|---|---|---|---|---|---|---|---|---|---|---|---|---|---|---|---|---|---|
| | 1 | 1 | 2 | 3 | 1 | 2 | 3 | 4 | 5 | 6 | 7 | 8 | 9 | 10 | 11 | 12 | 13 | 14 | 15 | | |
| SOC | Build ID 38 | | | Canister/Fill ID 40 | | | | | | | | | | | | | | Parity | Check Sum | EOC |
| 0x0A | 0x80 ~ 0xE3 | | | 0x20 ~ 0x7E (Exception 0x7C) | | | | | | | | | | | | | | 0x30 ~ 0x39 | 0x30 ~ 0x39 | 0x03 |

MEDICATION MANAGEMENT SYSTEMS AND METHODS FOR HEALTH AND HEALTH-RELATED FACILITIES

CROSS-REFERENCE TO RELATED APPLICATIONS

This application is a continuation of U.S. patent application Ser. No. 16/259,716 filed Jan. 28, 2019 and entitled "MEDICATION MANAGEMENT SYSTEMS AND METHODS FOR HEALTH AND HEALTH RELATED FACILITIES," which is a continuation of U.S. patent application Ser. No. 15/050,460 filed Feb. 22, 2016 and now issued as U.S. Pat. No. 10,192,035 and entitled "MEDICATION MANAGEMENT SYSTEMS AND METHODS FOR HEALTH AND HEALTH RELATED FACILITIES," which is a continuation of U.S. patent application Ser. No. 13/085,298 filed Apr. 12, 2011 and now issued as U.S. Pat. No. 9,268,912 and entitled "On Site Prescription Management System and Methods for Health Care Facilities," which claims priority to U.S. Provisional Patent Application No. 61/323,125 filed on Apr. 12, 2010, and entitled "On Site Prescription Management System and Methods for Health Care Facilities," all of which are hereby incorporated by reference for all purposes.

TECHNICAL FIELD

The disclosure generally relates to medication delivery in health and health related facilities using automated pharmacy dispensing systems and more particularly to automated medication prescription and dispensing, inventory management and control, and information processing in facilities including but not limited to resident health care facilities such as nursing homes, assisted living centers, retirement homes and senior communities with health care facilities, long term care facilities, prisons, and the like.

BACKGROUND

Management of automated prescription medication delivery in a resident health care facility, which may be referred to generally herein as a long term care facility or LTC, particularly those with in-house pharmacies and/or dispensaries involves multiple participants and a variety of complex operations. These include communicating prescriptions, dispensing medications as directed and on time, keeping accurate and timely records of the medications dispensed, receiving new and replenishment prescriptions into a facility or pharmacy-controlled management system, processing payment for the medications from a variety of providers, managing and tracking the inventory of drugs to be dispensed, providing accurate and timely feedback about the dispensing and actual administration of the medication, stock levels and rates of dispensing of the items in inventory, scheduling and requesting reorders, managing and monitoring of controlled substances, performing drug interaction and allergy analyses, all with little or no centralized control system to facilitate management and ensure compliance with regulatory and standard operating procedures required for these diverse operations.

These tasks must be performed accurately and efficiently to ensure safety and security of the patients and their medications, and minimize loss and waste of controlled substances and unused medications.

Traditional pharmaceutical delivery systems that employ written and spoken communication of information and hand-carried delivery are frequently characterized by very substantial inefficiencies and opportunities for errors, occasionally with grave consequences. At nearly every step of the way from writing a prescription, getting it filled and records generated, delivering it to a long term health care facility and providing for administration of the medication at the appointed time to the correct patient, opportunities for mistakes abound because the process involves numerous people handling the records and the medication for each instance of delivery and administration to fulfill the prescription. Further, the flow of information associated with management of the process takes place slowly, in serial fashion, and involves frequent handling of paper records.

In recent years a number of systems have been developed for use in various kinds of in-patient or resident health care facilities to automate the process. Automated dispensing machines have been developed to package and dispense medications to personnel tasked with administering the medications to patients on predetermined schedules according to the "script," the instructions accompanying the prescription. Portions of the process may be brought under computer control to manage the flow of information. Although computers are used to a substantial extent to handle the volume of data associated with dispensing prescription medications, the control and packaging of the medications, the patient records for the medications prescribed by physicians, processing payment by third parties, etc., inefficiencies and the opportunities for errors and substantial waste remain.

One ongoing problem in many systems is the amount of time delay that occurs from the instant a prescription is issued by a physician until the initial dose is dispensed and administered to the patient. The consequences of delay and errors in administering the drugs prescribed can be serious and even catastrophic. Accordingly there is a need for system and methods that minimize this delay and include controls that minimize error in the processes involved in the delivery, management, dispensing and administering the medications.

Another problem with conventional systems is the lack of timely feedback regarding the status of processes at each step from incoming prescription to administering the prescribed dose at the appointed time, and the inability of conventional systems to operate in a forward-looking mode, that is, to know what medications are needed in the future according to present prescriptions so that inventory levels may be regulated and medications reordered and distributed to patient locations before an out-of-stock condition occurs. Present systems are "reactive," that is, they are designed to react to out-of stock or par level conditions. A consequence of the reactive operation is that residents may have to go without a dose at the prescribed time because the medication was not dispensed on time due to an out-of stock condition caused by sudden increases in usage or improper inventory control. A missed dose can have serious consequences to some residents or patients. Thus, what is needed is a "proactive" system that knows when a supply of a medication will be emptied and provides for distribution of the replenishment on a schedule that maintains the dispensing of the medications in an uninterrupted flow, even in instances of sudden increases in usage.

A related problem with conventional systems is the opposite condition when the processes of dispensing medications are not sufficiently controlled—i.e., inventory levels are not well-matched to prescription requirements or the tracking of medications dispensed and administered is insufficient. The result is substantial quantities of medications that are not administered and must be discarded because, for safety and security reasons, there is no provision for re-stocking the unused medications. This circumstance causes waste that requires controlled procedures for destruction of the unused substances. Elimination of such waste would result in reduced costs to the long term care facilities, resident patients and their families, insurance providers and taxpayers, and enhance both safety and efficiency of the prescription process.

Yet another deficiency of existing systems is an inability of various stations or functional entities of the system to interact with each other or to be organized so that their functional operations are coordinated to minimize lost opportunities to respond to current and anticipated conditions because prescription data is not available or the status of a dispensing process is not known, etc. Accordingly there is a need for synchronizing the operations and processes in the system so that process flows make use of all available data and are coordinated with each other to ensure efficient and accurate dispensing and administering of medications. Especially important would be the ability to provide direct communication between prescription and order entry and the dispensing processes and apparatus, and the dispensing apparatus and the records associated with dispensing and administering of the medications.

While the use of automated packaging and dispensing machines located in the long term care facility or pharmacy may provide some efficiencies, and alleviate some of the bottlenecks, unless they are used to maximum advantage, few of the aforementioned problems are actually solved. The problems are more in the nature of information flow than automating some portion of the packaging or handling of prescription medications. In one example the data that defined the identity and contents of each canister in a dispensing machine occupied more than two kilobytes of data. One typical example of this prior art technique is illustrated in FIG. 1, which depicts the layout of the canister memory space 10 having a first row 12 specifying the byte population of the memory, a second row 14 identifying the data stored in the memory 10, and a third row 16 defining the hexadecimal address of the various items of data. Of interest are the data sections of the second row: canister ID 18 (3 bytes), the Chip ID 20 (15 bytes), and, most significantly, the Chip Memory Data 22 that describes the prescription medication contained in the canister (more than two kilobytes). When two kilobytes of data is multiplied by several hundred times—the number of canisters in a typical dispensing machine—the processing time takes on significant dimensions, becoming a substantial cause of processing delay, and dispensing errors due to the delay in processing the data in the prescription processing and dispensing operation.

In another example of the problems encountered when using automated packaging and dispensing machines, consider that in such systems the containers from which the medications are dispensed, often called canisters, must be available in a variety of sizes and configurations, each adapted to a particular physical size and shape of a medication unit, pill, or tablet. The result is each medication can only be contained in one configuration of canister. Some medications having the same formula are available in multiple sizes and shapes; others in only one size and shape; still other generic forms of the same drug, available from different manufacturers, may require a variety of different configurations. Further, the size and shape of medications are subject to change. This variety of configurations complicates the process of determining the most efficient container or canister configuration. The result can be inefficiency and compromise, which is wasteful of resources, more susceptible to errors, and often wasteful of medications because accommodating this variety is cumbersome, time-consuming, and expensive.

SUMMARY

Accordingly there is provided a system for controlling dispensing of medications in a health care facility coupled to a network, comprising: an order management system (OMS) and an associated database operating on a hosted (central) remote server coupled to said network, said OMS serving said health care facility via said network; a prescription order entry (POE) system coupled via said network to said order management system; a medication dispensing system installed in said health care facility and coupled via said network to said order management system; and an electronic medication administering record (eMAR) coupled through said medication dispensing system via said network to said order management system.

In another embodiment a method is provided for automated dispensing of prescription medications to one or more health care facilities via associated remote pharmacies, comprising the steps of: providing a central hosted remote server having a system database and coupled to a network and operating an order management system (OMS) containing interface links to a plurality of remote operative units; providing at least one medication dispensing system in each health care facility, wherein each said medication dispensing system includes an automated prescription drug packaging and dispensing machine (ADM) and a work station coupled thereto, and each said automated dispensing machine (ADM) is coupled to said central hosted server; coupling a prescription order entry system (POE), accessible from said health care facility, to said central remote server via said network; including in said automated dispensing machine (ADM) a plurality of medication canisters for storing and dispensing prescription drugs therefrom; and associating with each said canister a memory device having a storage capacity not exceeding 48 bytes.

Further, a system for control of prescription drug dispensing is provided comprising: a database and a prescription order entry (POE) system coupled respectively via a network to an order management system (OMS), said OMS serving an in-patient health care facility via said network; an automated drug packaging and dispensing machine (automated dispensing machine or ADM) installed in said health care facility and coupled to said OMS; and an electronic medication administering record (eMAR) coupled to said OMS through said automated dispensing machine.

In other aspects, the automated dispensing machine comprises a cabinet containing a plurality of individually removable canisters for storing an inventory of prescription medications selected according to resident's needs; a processor responsive to communication with said OMS and said eMAR and configured for control of said canisters; and a canister memory associated with each canister and accessible to said OMS and said eMAR, said canister memory location containing a build code ID and a canister fill ID, wherein said build code ID comprises a code representing a particular medication and a species thereof, and said canister fill ID comprises a code representing said canister and a suffix code representing each instance of filling said canister.

In another aspect, the system further comprises a mechanism for packaging a medication for a patient and a mechanism for dispensing said medication to a patient care worker.

In another aspect, the system further comprises a computing device having a display and data entry provision for requesting dispensing of and recording administration of a prescription medication to a resident patient.

In another aspect, the computing device further comprises a scanning device for reading an encoded label.

In an alternate embodiment, a method is provided for dispensing prescription drugs in a health care facility, comprising the steps of stocking an automated dispensing machine (ADM) installed at said health care facility and linked to an order management system (OMS); entering patient prescription information into a prescription order entry (POE) system in communication with said order management system; compiling a comprehensive patient medication record in an electronic medication administration record (eMAR) contained in a handheld eMAR device coupled to said ADM; and linking said eMAR through said ADM to said OMS.

In another aspect, the method comprises the steps of updating said eMAR with each dispensing operation from said ADM; and updating a database coupled to said OMS according to said eMAR.

In another aspect, the method comprises the step of updating a re-order queue according to said data stored in said database coupled to said OMS, including scanning label information from said eMAR device for entry into said eMAR.

In yet another alternate embodiment, a method is provided for reducing delay in processing item data in an inventory control system, comprising the steps of formatting a data transfer message to exclude said item data to be transferred; limiting the contents of said data transfer message to a build code identification statement and a canister fill identification code statement; and storing said item data to be transferred in a database location identified by said build code statement, wherein said build code identification (ID) comprises a code representing a particular stock item and a species thereof, and said canister fill identification (ID) comprises a code representing said canister and a suffix code representing each instance of filling said canister.

In an alternate embodiment a method for coordinating the processing of data items among participating entities in the system wherein the data being processed is synchronized by a combination of user tokens (who), data identifiers (what), and unique Ids for the entities in the system (where).

DESCRIPTION OF THE FIGURES

The accompanying drawings facilitate an understanding of the various embodiments:

FIG. 1 illustrates one example of a prior art memory format for prescription medications;

FIG. 2 illustrates an example of a more efficient memory format for a prescription medication according to at least a first embodiment as disclosed herein;

DETAILED DESCRIPTION

Figure 3:
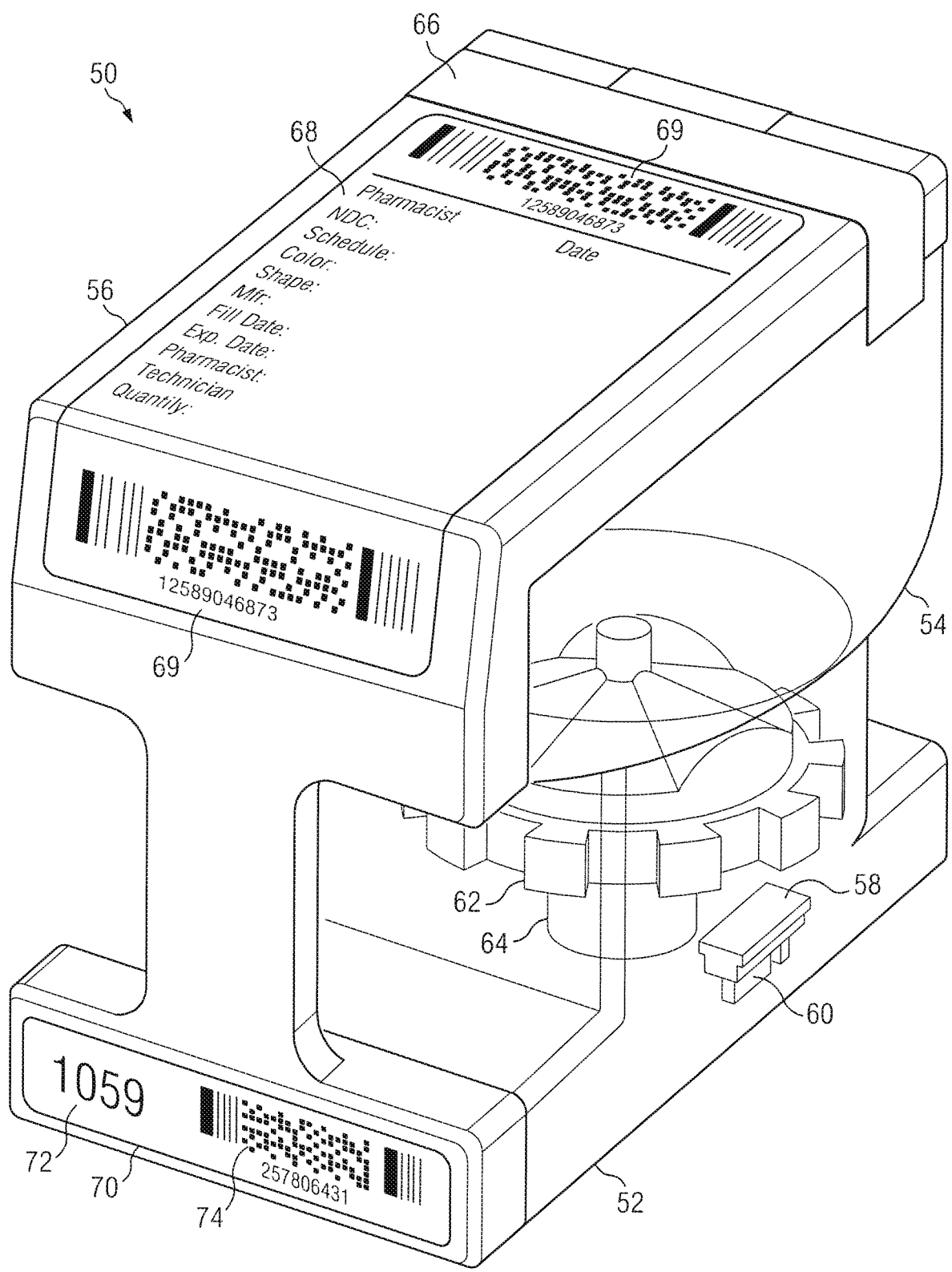
FIG. 3 illustrates a front perspective pictorial view of a medication canister for a dispensing machine for use in at least the first embodiment as disclosed herein.

In the following detailed description of the present invention, various structural components illustrated in the drawings will be identified by a reference number. When the same component appears in more than one figure, the same reference number will generally be used. However, in some cases, such as when the embodiment is a different one, a different reference number may be used in a particular drawing. The description is to be read in conjunction with the drawings. The term health care facility as used herein may mean any facility that provides health care. The facility may include dispensing of medications to patients or residents of the facility. Examples include long term care facilities, nursing homes, prisons, certain hospitals, retail facilities, and the like. The term "dispensing machine" is used synonymously with "automated prescription drug dispensing machine" and "automated dispensing machine (ADM)."

The invention to be described herein concerns automated pharmacy dispensing systems and methods. Disclosed herein are a number of distinct embodiments including: (1) a system for control of prescription drug dispensing comprising a novel combination of an automated prescription drug packaging and dispensing machine in a health care facility plus off-site management and control coordinated by a main server coupled via a global communications network to the operating entities in the system; (2) a method for dispensing prescription drugs in a health care facility, that is, the use of the novel system identified above; (3) a method for reducing delay in processing data in a prescription drug order and dispensing system of a health care facility that relies in part on re-defined contents of data that is incorporated into each canister installed in the packaging and dispensing machine of the system; and (4) a method for coordinating or synchronizing the operating entities in the system with respect to the data being processed during the operation of the above prescription drug dispensing system. The synchronization system ensures that all entities in the system, including the stations or kiosks in the health care facilities connected to the network, are operating on the correct data. In addition, (5) the system is fully scalable and can accommodate multiple health care facilities, multiple pharmacies, and multiple automated dispensing machines in each health care facility.

Figure 5:
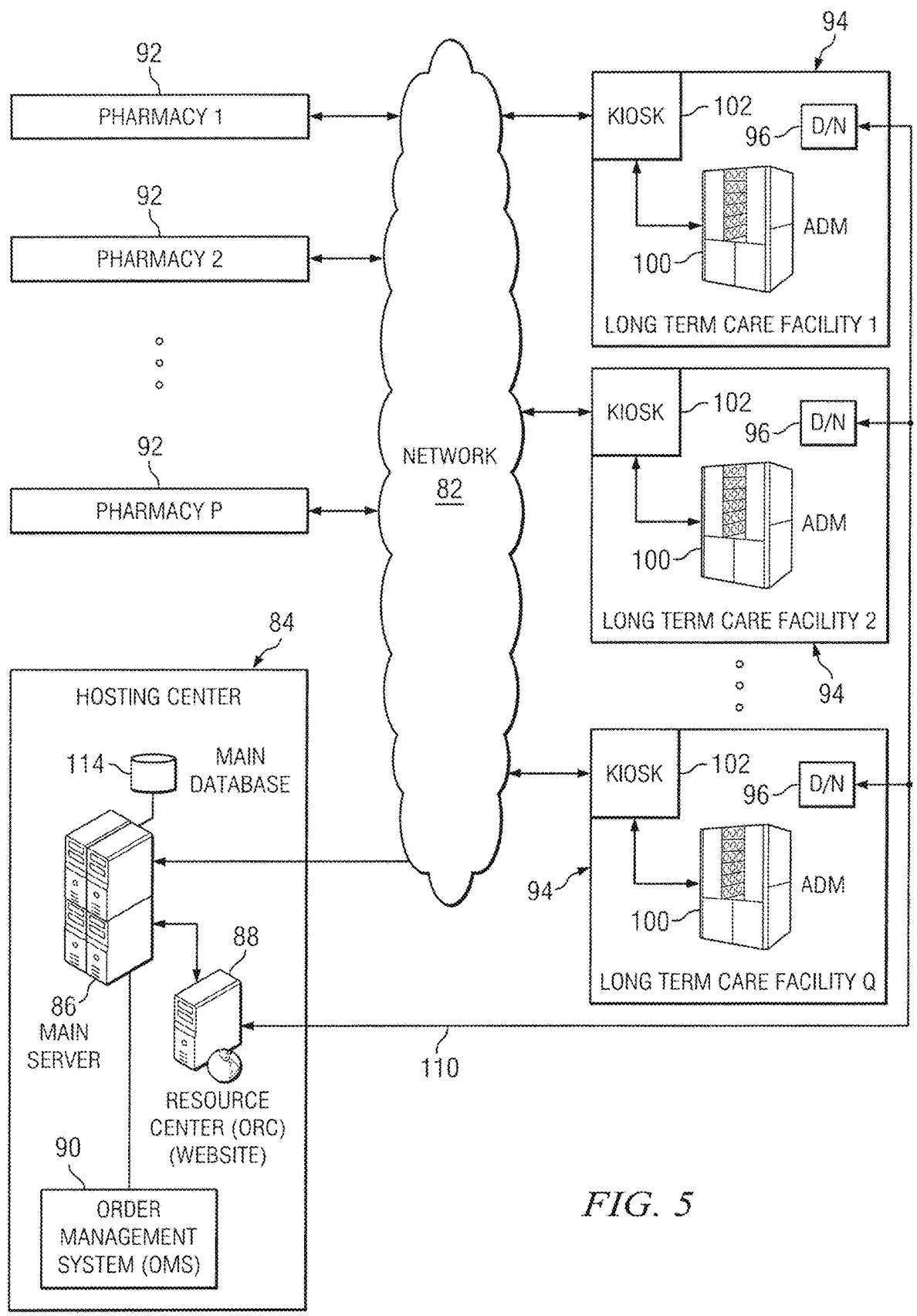
FIG. 5 illustrates a general system block diagram according to one embodiment disclosed herein.
Figure 6:
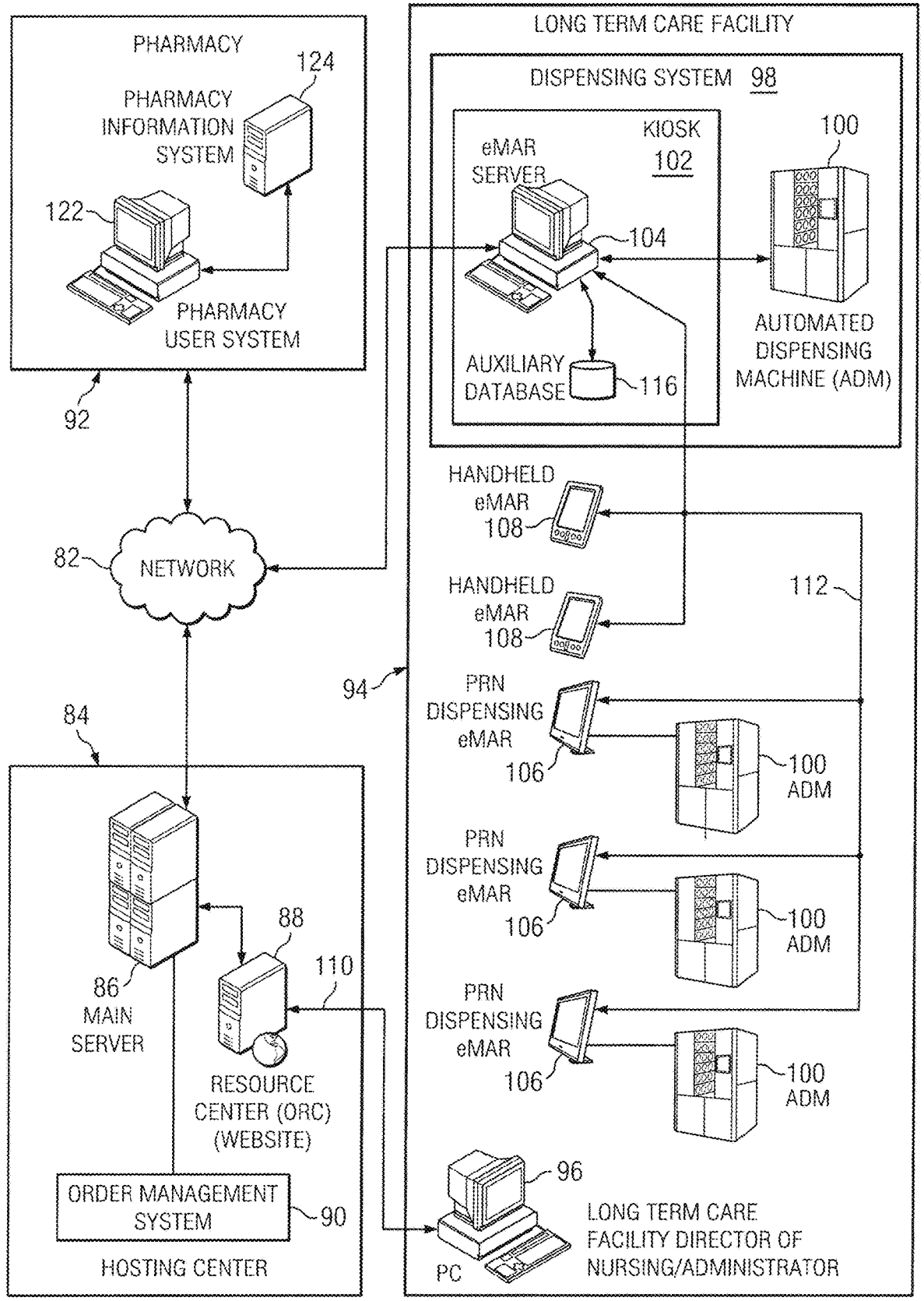
FIG. 6 illustrates a system block diagram according to a variation of the embodiment of FIG. 5.
Figure 7:
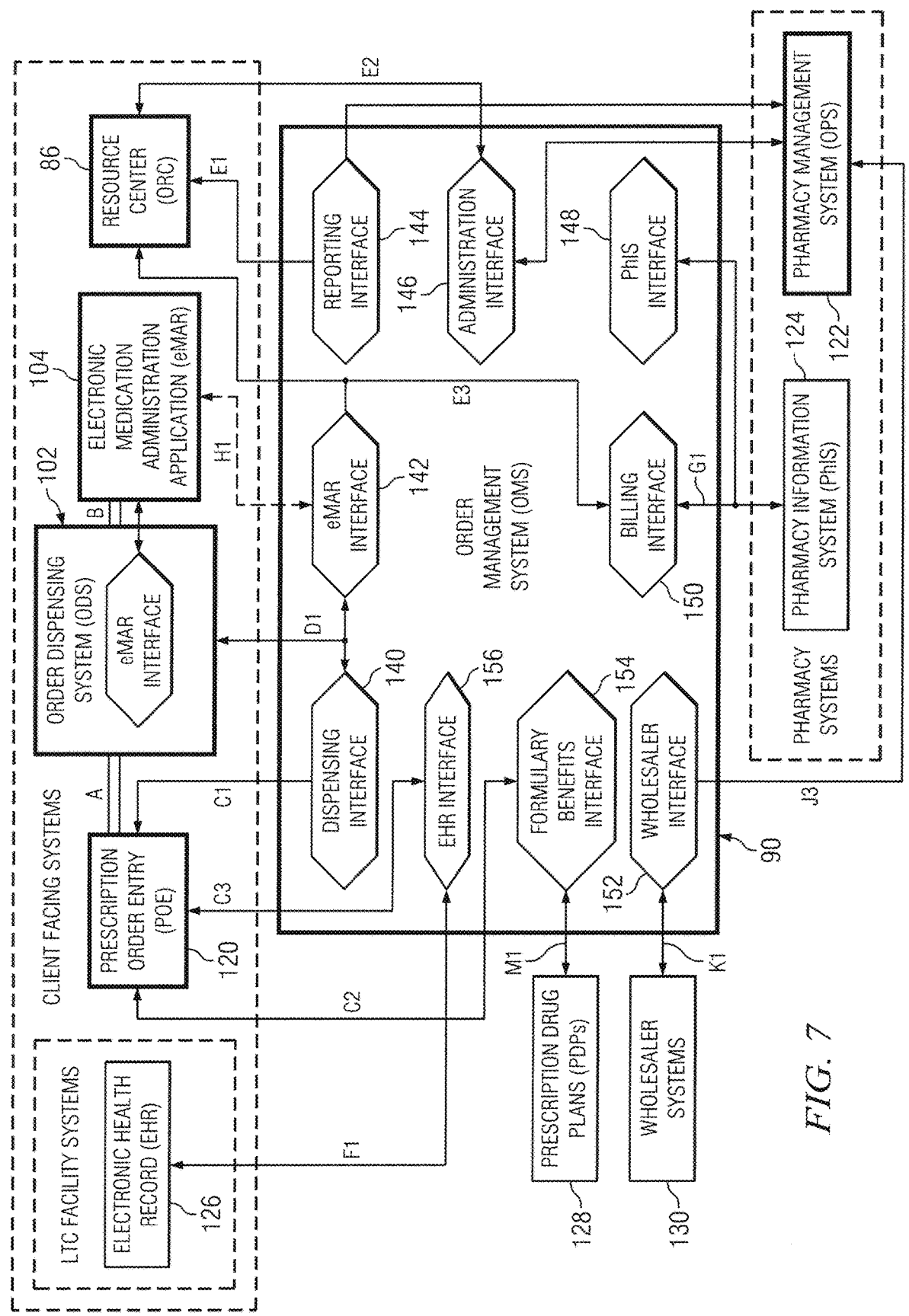
FIG. 7 illustrates a system block diagram of the basic architecture of one embodiment disclosed herein.
Figure 8:
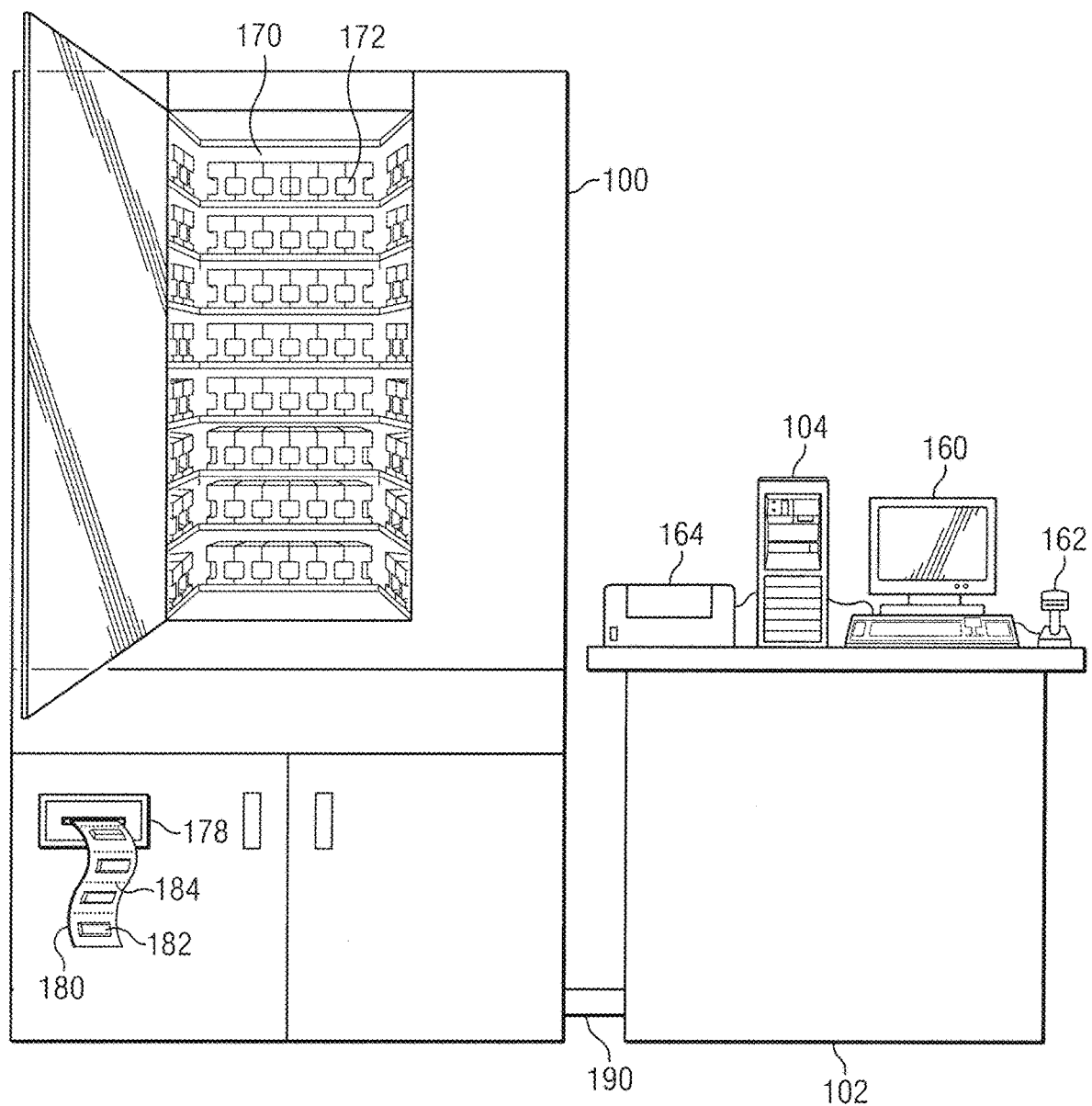
FIG. 8 illustrates an automated prescription dispensing machine and an associated work station disclosed herein, for use with the embodiments of FIGS. 2 through 7.

In a first illustrative embodiment, the overall system is illustrated in schematic block diagram form in FIG. 5, which shows the basic structure of the system as depicted by its primary operating components. In general, the system may accommodate multiple health care facilities such as long term care facilities (LTCs) and pharmacies, all connected to a main server operated by a hosting center as a typical example. FIG. 6 presents a similar schematic block diagram showing the structures of the long term care facilities and the pharmacies, and the functional relationships among the operating entities and components of the system. FIG. 7 illustrates in block diagram form the architectural relationships of the functional components of the system. As will be explained, the portions of FIG. 7 having a bold line outline depict new structures created specifically for the present invention. FIG. 8 depicts a prescription drug dispensing system that includes one form of an automated prescription drug packaging and dispensing machine, which will often be referred to as an automated dispensing machine (ADM) herein, and a kiosk or work station equipped with a PC or server, a scanner, and optionally, a printer.

Figure 9A:
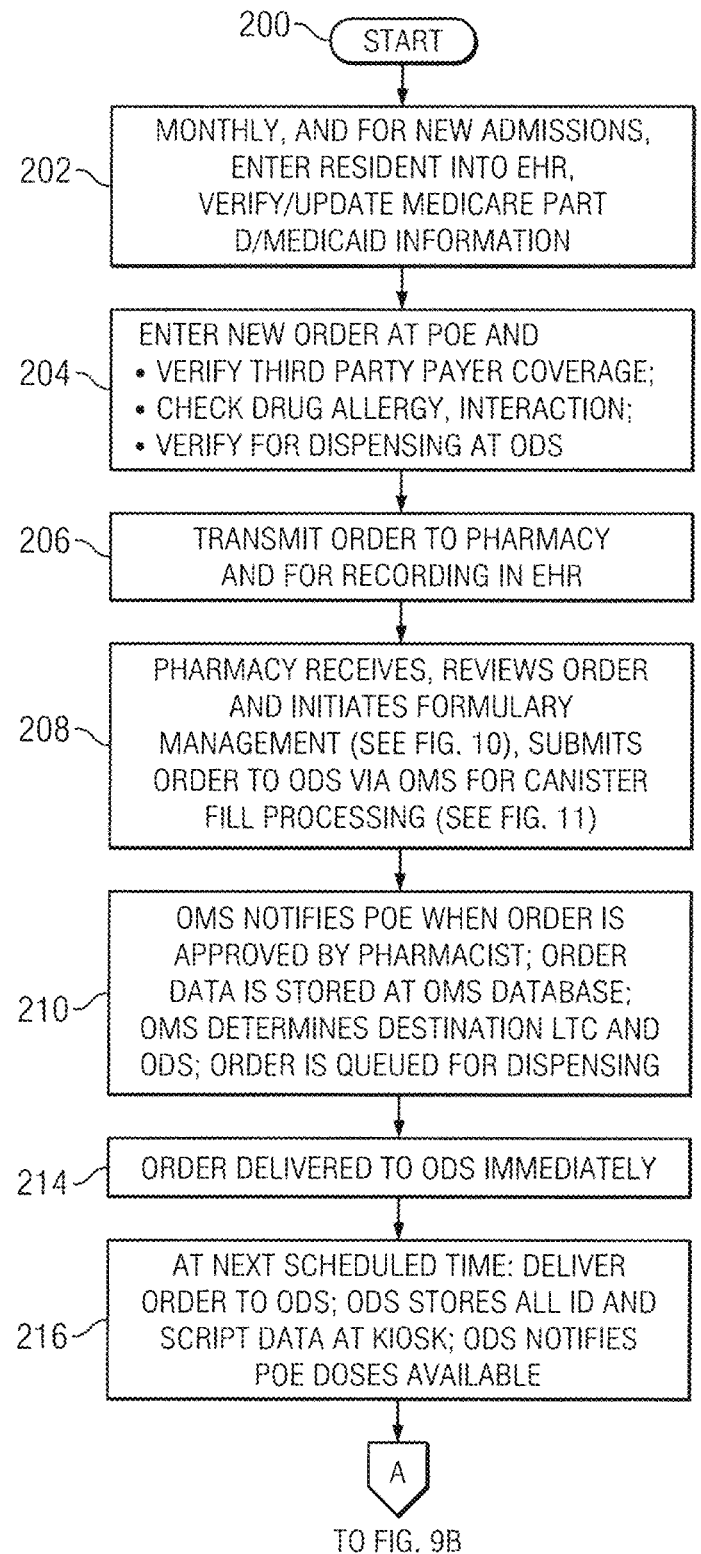
FIG. 9A illustrates a first portion of a flow chart for the basic operation of the system of FIGS. 6 and 7.
Figure 9B:
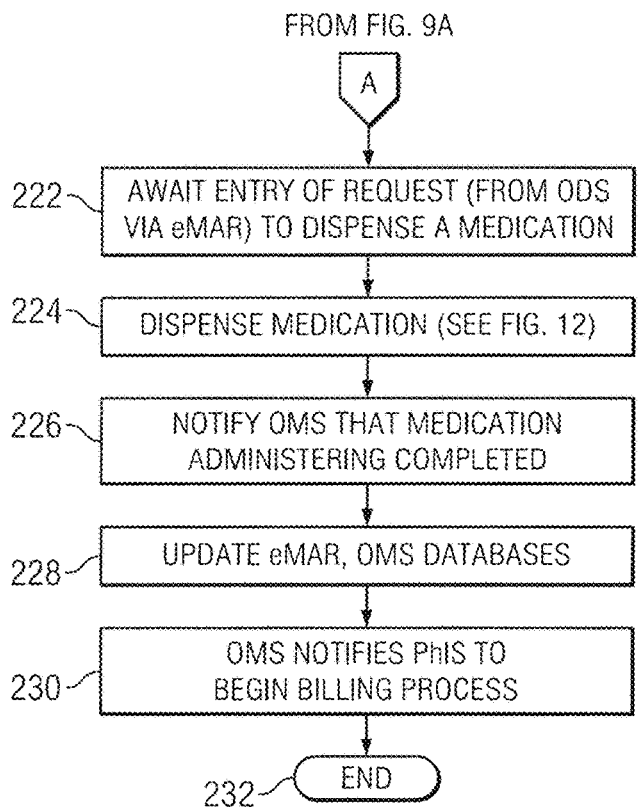
FIG. 9B illustrates a second portion of the flow chart for the basic operation of the system of FIGS. 6 and 7.

In a second embodiment, FIGS. 9A and 9B depict a basic operation of the system. FIGS. 10 through 14 illustrate other basic aspects of the methods of using the system of FIGS. 5, 6, 7 and 8 to dispense prescription medications in a health care residence or facility. Some of these operating relationships may be understood by referring to FIGS. 11A through 11F. Several specific communicating links and signal flows in FIG. 7 that represent new flows of information in pharmaceutical management processing systems are depicted by highlighted lines.

In a third embodiment shown in FIG. 2, reduction of the data content of the canister memory chip to the combination of a build code ID and a canister fill ID, each requiring only relatively small amounts of data, enables a very substantial reduction in processing time resulting in much less inherent delay in processing the system inventory, the tracking of dispensing problems, and the dispensing of prescriptions and prescription information. The canisters themselves are described in FIGS. 3 and 4, and the process of using the modified canister system is illustrated in FIG. 8. Detailed data regarding the prescription drug information associated with the build code ID and the canister fill ID is stored in the main database accessed by the management system and referred to only as needed.

The build code ID may comprise a four digit code representing the structural configuration (stored in a database) of the canister that is compatible with a particular group of medications. Medications are supplied in a large variety of forms, sizes, shapes, etc. ("attributes"). The structural components of each canister are adapted to accommodate a particular group of such attributes. The canister fill ID may comprise a 12 digit code that uniquely identifies the canister. In one example, the code may represent when (the date and time) the build code ID is first assigned and a three digit suffix code representing each instance of filling said canister with said medication. Other data associated with the canister fill ID may be stored in a database location corresponding to the canister fill ID. Other code types or length for the build ID and canister fill ID codes may be used in variations of the exemplary embodiment described herein.

In a fourth embodiment, a method for coordinating data being processed by the various entities in the system is provided through assignment of ID information to enable synchronization of the data of the various stations on the network as needed. It is this coordination process that enables the system communication efficiencies leading to substantially improved processing speed and the ability to proactively manage the forward-looking inventory control aspects of the system.

Beginning with the detailed description, FIG. 2 illustrates an example of a more efficient canister memory format for a prescription medication according to at least one embodiment disclosed herein. The figure depicts the layout of the canister memory space 30 as disclosed herein having a first row 32 specifying the byte population of the memory in each of the identified groups, a second row 34 describing the data content stored in the memory 30, and a third row 36 defining the hexadecimal value ranges of the various items of data. Of interest are the data content sections of the second row: a Build ID 38 (3 bytes), and the Canister/Fill ID 40 (15 bytes). It is important to notice that the "Chip Memory Data 22" of the prior art, which used in excess of 2,000 bytes of data is no longer stored in the canister memory 30. This is because the inventor realized that such detailed information about the prescription drug contained in the canister, which occupied more than two kilobytes of data, no longer needed to be stored in the canister itself. This data may be stored in a database location and accessed as needed outside the most important real time sequences for operation of the system as will be subsequently described. The result of this insight is a very substantial reduction in processing time leading to a major improvement in efficiency and responsiveness of the system to the needs of the health care facility.

FIG. 3 illustrates a front perspective pictorial view of a medication canister for an automated prescription drug dispensing machine (ADM) for use in the illustrative embodiment of the present invention. The canister 50 may be assembled from interchangeable parts including a transparent main body 52 that includes a transparent hopper section 54, a lid 56, a memory receptacle 58, a memory chip 60, a division block 62 with drive hub 64, and a security tape 66. The division block 62 is a rotating distributor that indexes one position for each medication pill, tablet or capsule to be dispensed. The rotation is provided by a drive mechanism within the dispensing machine to be described that is coupled to the drive hub 64. The drive hub 64 has an internal spline to engage the drive shaft of the dispensing machine in a non-slip manner. The engagement of the drive shaft and the splined drive hub 64 occurs when the canister 50 is selected for dispensing and moved into position in engagement with the drive mechanism. Others of the interchangeable parts of the canister 50 will be described for FIG. 4.

The canister 50 may include a detailed medication fill label 68 attached to the lid 56 of the canister with printed specifications of the prescription drug medication and a machine-scannable portion of information 69 such as a bar code or the like. The canister fill label 68 may further include a duplicate machine-scannable portion of information 69 wrapped over the upper front edge of the canister as shown to enable scanning the label when the canister is installed in a dispensing machine. The canister may further include a build label 70 that has a four digit build code 72 and bar coded build information 74. The build label 70 is preferably printed when the canister 50 is constructed and may be permanently affixed to the canister 50 throughout its life. The build information is scanned whenever the canister is handled so that the system always knows the identity and location of the canister and can thereby reference its contents with database information whenever the build label 70 is scanned. The medication fill label 68 is preferably printed and affixed to the canister 50 each time the canister is prepared for installation in an automated dispensing machine. Locating the scannable build code label 70 on the front, handle portion of the canister facilitates rapid identification and logging of the canister regardless of where it is in the system or how it is being handled. The canisters are prepared in a pharmacy, which may usually be located at the health care facility or off-site, following any maintenance on the canister before use or reuse. Maintenance may include removal of old labels, replacement of worn or broken parts, inspection, cleaning, etc. before restocking for reuse. In some cases the canisters may be modified or configured to accommodate different medication attributes—that is, different form, shapes, and sizes of the tablet, pill or capsule that will be stored therein for dispensing. A new build ID is assigned to the canister when it is reconfigured.

Figure 4:
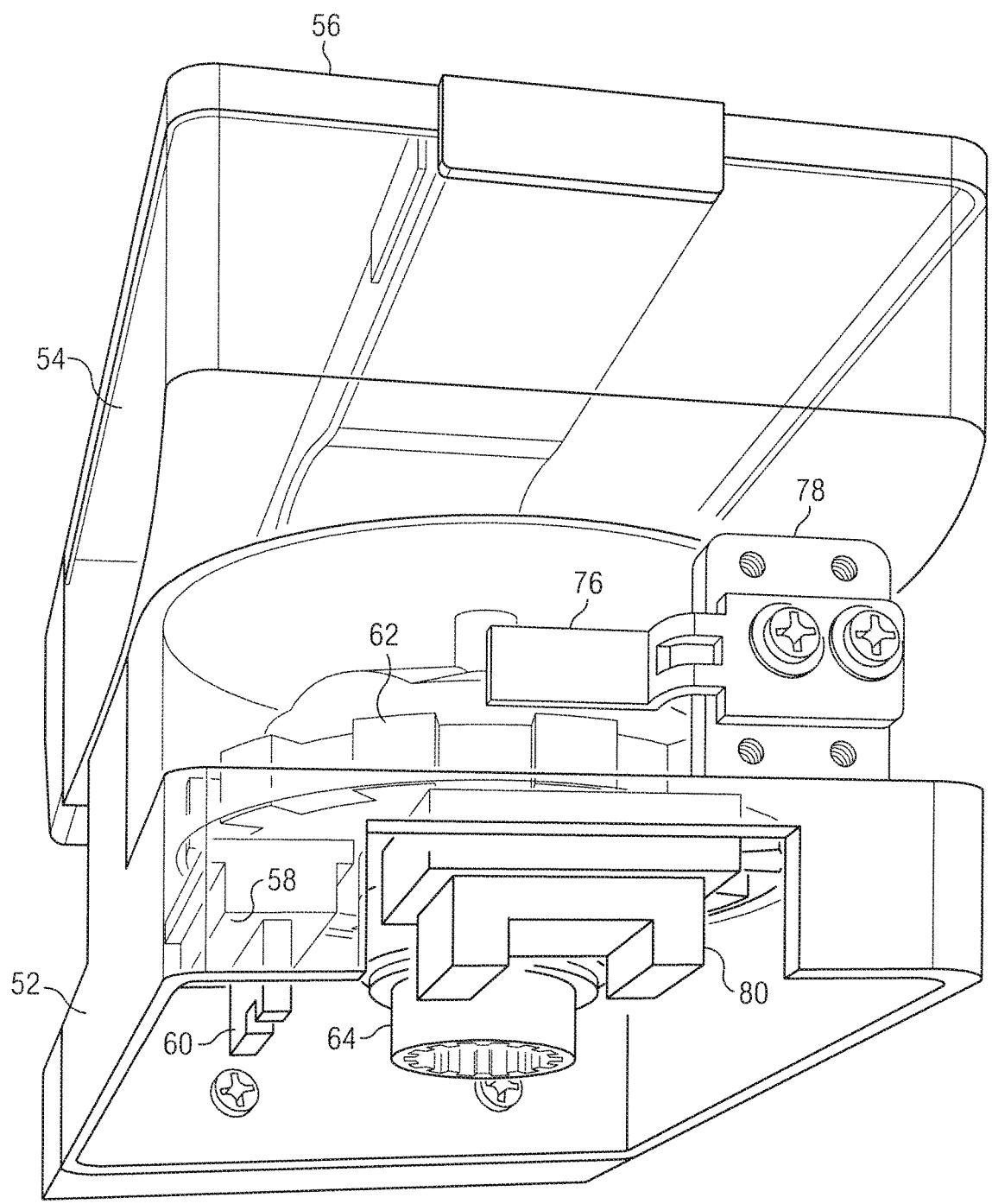
FIG. 4 illustrates a rear perspective pictorial view of the medication canister of FIG. 3.

FIG. 4 illustrates a rear perspective pictorial view of the medication canister 50 of FIG. 3. In this view from slightly below the canister 50 the main body 52, transparent portion 54 and lid 56 remain visible, along with the division block 62, the drive hub 64, the memory receptacle 58 and the memory chip 60. The memory chip 60 may preferably be a printed circuit board component having connection traces on one of both of its faces for mating with corresponding conductors when inserted into a receptacle as the canister is installed in the dispensing machine. Thus, the memory chip 60 is connected into the circuitry of the dispensing machine so that its contents may be read during operation of the machine to access the canister (i.e., bring it into a dispensing position), dispense a unit (or the required number of units) into a package, and arrange the packages in a predetermined sequence for dispensing to the person who will administer the medication to the resident intended to receive the unit(s) of medication. Although this process is generally operated under programmed control the facility may dispense medications whenever it chooses, for example in PRN or demand circumstances.

Also visible in FIG. 4 are a partition 76, a partition fix block 78, and a guide block 80. The partition 76 is a flexible arm, fixed to the fix block with screws as shown. The fix block 78 includes several threaded holes to permit adjustment of the partition 76 in a vertical direction relative to the lower portion of the division block 62. The flexible arm includes a small tab (not shown) on the side of the partition 76 facing the division block 62 and acts to assist in dispensing a unit of medication during operation of the dispensing machine. The guide block 80 is fixed to the underside of the main body 52 of the canister and acts as a key to locate in the transport mechanism (not shown) of the dispensing machine. The transport mechanism can accommodate several different sizes (capacities) of canisters, each with its own keyed receptacle to match the guide block 80 of the appropriate canister 50. The interchangeable parts of a canister 50 may include at least the main body 52, the division block 62, the partition 76, and the guide block 80.

The canisters illustrated in FIGS. 3 and 4 may generally contain a 10 to 30 day supply of prescription medications of an individual resident or patient of a health care facility. The quantity of medications depends strongly on their costs, so the costs of maintaining an inventory is an important consideration. The system may accommodate supplies of up to 90 days if needed. In one alternative, for example, a canister may contain a larger quantity of medications of a type to be dispensed to more than one resident in an area served by the dispensing machine. The dispensing machine provides for secure storage, convenient packaging, and accurate dispensing of prescription medications on schedule, "STAT" (immediately), or on demand (also referred to as "PRN" or as the resident or patient requests), automatically or under computer control, under the supervision or administration of a director of nursing in the typical facility.

FIG. 5 illustrates a general system block diagram according to one embodiment of the present invention. A hosting center 84 is shown that includes a main server 86 and a resource center (ORC) 88. The main server 86 operates an order management system (OMS) 90. The main server 86 further includes a main database 114 coupled thereto. The order management system 90 is a comprehensive software system that runs on the main server 86 and includes a suite of interfaces to a number of other functional units of the system, in addition to the communications and other housekeeping operations provided for in the order management system 90. The main server 86, order management system 90, and database 114 together form the operating hub of the prescription drug ordering and dispensing system of the present invention. The resource center 88 is coupled to the main server 86 and provides a website presence for the functional units of the system to deposit and obtain information concerning operations of the system. These units typically are located in the hosting center 84, which in general may be provided by firms outside of and not otherwise connected or related to the health care facilities or pharmacies participating in the dispensing system described herein.

Communication between the main server 86 and the functional operating units of the system occurs in the illustrative embodiment through connections to a global communications network 82 such as the Internet. The other principal functional operating units of the system coupled to the network 82 include one or more pharmacies 92, designated as pharmacy 1, pharmacy 2, etc., and pharmacy P; and one or more long term care (LTC) facilities 94, designated similarly as LTC 1, LTC 2, etc., and LTC Q. Long term care facilities 94 have been selected in this exemplary system to illustrate the principle concepts disclosed herein. Persons familiar with the prescription drug processing and delivery systems in current use will appreciate the generality of the concepts described herein and recognize their applicability to other types of resident health care facilities such as nursing homes, assisted living centers, rehabilitation facilities, and even prison systems where health care is provided. All of these functional operating units coupled to the network 82 are equipped with communications interfaces to enable the required exchanges of data and commands for the system to perform its operations.

Each LTC facility 94 preferably includes a director of nursing or administration 96, which may be represented by a workstation PC (not shown), an automated prescription drug dispensing machine (ADM) 100, and a kiosk 102 coupled directly to the ADM 100. As will be described, the kiosk 102 may be a workstation having a PC with display and a scanning device, and perhaps a server, database, printer, etc. in each LTC 94.

FIG. 6 illustrates a system block diagram according to a variation of the embodiment of FIG. 5, wherein further details of the pharmacy 92 and a long term care facility 94 in a typical system according to the present invention are illustrated. The network 82 and the hosting center 84 containing the operating units of the main server 86, database 114, resource center 88, and the order management system 90 are as illustrated in FIG. 5. The pharmacy 92 in this embodiment may include a pharmacy management system 122 and a pharmacy information system 124, each coupled to the other and operated by software applications residing on their respective PCs or server. Each of these units may be independently coupled via the network to the main server 86 as will be described. The operative portion of the long term care facility 94 is its prescription drug dispensing system 98. The dispensing system 98 includes the automated dispensing machine 100, the kiosk 102 coupled to it that may include an eMAR server 104 operating on the kiosk, along with the other components mentioned for the embodiment of FIG. 5, including an auxiliary database 116, a work station with display, a scanning device, etc. FIG. 6 also depicts a LTC Director of Nursing work station 96, which may be coupled directly to the resource center website 88 via a link 110 through the network 82. A long term care facility 94 may include a plurality of automated dispensing machines 100, each under the control of a respective kiosk 102 or a PRN dispensing eMAR 106—a laptop PC or handheld computer (alternately, slave kiosk)—as shown, each of which is connected to the eMAR server 104 at a kiosk 102 via a local communications bus 112, which may be internal to the dispensing system 98. Connected to the same communications bus 112 may be additional handheld or tablet PCs 108. These multiple ADMs 100 and PCs 106, 108 may be needed in larger resident patient facilities. Thus, the system can be scaled to include operation with a plurality of dispensing machines 100 from, for example, a single kiosk having a workstation or eMAR server 104, auxiliary database 116, scanning device, etc., as illustrated and will be more fully described regarding FIG. 8 herein below.

FIG. 7 illustrates in schematic form a system block diagram of the basic architecture of one illustrated embodiment disclosed herein. The units represented by block outlines are essentially software providing various functions operating within the system, including communication of data via their respective connections to the network 82 as described. Functional units depicted as a block having a bold outline contain software written especially for the present invention. Further, it will appreciated that the order management system 90 is an essential and central piece of the system because it provides the overall management and control of the system; that is, it integrates the functions of all the operating units connected to the order management system 90 into the seamless operation necessary to provide an efficient and responsive prescription drug dispensing system that overcomes the inefficiencies and inadequacies of the prior art dispensing methods. These advantages will become apparent in the description that follows. The software of the various operating units runs on various PCs or servers as described for FIGS. 5 and 6. In one section of FIG. 7 several functional units are surrounded by a dashed line and designated "Client Facing Systems." This means these units are located in or accessible from the long term care facilities 94 via the network 82. Other functional units are located in a pharmacy system 92, which may be located either outside the long term care facility 94 or within the LTC facility. Still other functional units may typically be external to the system because they represent other entities with which the present system interacts, such as the prescription drug plans 128 and wholesaler systems 130.

Continuing with FIG. 7, the order management system 90 includes the following interface programs for communicating with the various external functional units in the long term care facility 94 (or facilities 94) or elsewhere. As shown in the drawing, each of these interface programs connects to communication links with other interface programs internal to the order management system 90, or with functional operating units outside the order management system 90 via communication through the network 82. These links are designated with capital letters and numerical symbols as shown in FIG. 7. A dispensing interface 140 is linked via the link C1 to the prescription order entry (POE) 120 and to the eMAR interface 142 respectively in the order management system 90 and the order dispensing system (ODS) 102 in the LTC 94 via a link D1. The eMAR interface 142 is further coupled with the eMAR functional unit 104 in the LTC via link H1 and also to the resource center (ORC) 86 and the billing interface 152 internal to the order management system 90 via the link E3.

Further in the order management system 90 is located a reporting interface 144 that is connected via the link E1 to the resource center 86 and via the link J1 to a pharmacy management system (OPS) 122. An administration interface 146 in the OMS 90 is connected via the link E2 to the resource center 86 via the link E2 and to the pharmacy Management system 122 via the link J2. The billing interface 152 is also connected via the link G1 to a pharmacy information system (PhIS) 124. The wholesaler interface 154 is shown coupled to the pharmacy management system 122 via the link J3 and to one or more wholesaler systems 130 via the link K1.

Continuing with the OMS 90 interfaces, a formulary benefits interface 156 is coupled via the link M1 with the prescription drug plans (PDPs) 128 and vis the link C2 with the prescription order entry functional unit 120. An electronic health record (EHR) 158 is connected via a link F1 and the network to an EHR 126 in the long term care facility 94, and to the prescription order entry (POE) unit 120 via the link C3.

The foregoing lines of communication identified by the letters C, D, E, F, G, and H (including C1, 2, 3; D1; E1, 2, 3; F1; G1; and H1) between the order management system 90 and the functional units across the network 82 form a combination not known to exist in the prior art. That is, management and control of these on site functional units in a health care facility, via communication over a network such as the Internet from an off-site main server 84 running a suite of software such as the order management system (OMS) 90 of the present invention is not known to exist prior to the invention thereof as disclosed herein. There are many benefits to this architecture as will become clear in the description which follows.

Further, the on-site communication links identified as the order entry bus A and the eMAR bus B, respectively connecting the order dispensing system (ODS) 102 with the prescription order entry unit 120 and the electronic medication administration record (eMAR) 104 form a structure unique to prescription dispensing system in use in resident health care facilities. These linked-together functional entities in the health care facility provide substantial enhancements to the efficiency and accuracy of the administration of prescription medications in health care facilities that provide health care to their residents in addition to their other basic needs. Providing the benefits of this novel combination of communication capabilities required substantial software innovation to overcome obstacles that have stood in the way of achieving these improvements until the insights leading to the present invention, even despite the existence of automated dispensing machines, which hereto fore had been limited to basic, stand alone operation requiring significant human intervention to ensure accurate and timely administration of medications, without the benefits of linking their operation to the other functional entities involved in the dispensing of prescription drugs under machine control.

FIG. 8 illustrates an automated prescription dispensing machine and an associated work station according to the present invention for use with the embodiments of FIGS. 2 through 7. Depicted in the drawing are an automated prescription drug dispensing machine 100 and a kiosk 102 coupled together by a communications bus 190 for conveying both control and data between these units. The kiosk 102, in one form as a cabinet but which could as easily be a desk or table, supports a workstation or PC 160 having a display and other well-known attributes of a PC. Connected to the workstation may be a scanning device 162 such as a bar code scanner as shown in the present illustrative embodiment. The scanning device 162 may be used for scanning encoded indicia printed on a canister label or a medication package label or any other identification data printed in documents, personnel ID cards or badges, for example. Other devices having the ability to scan and read an image (visual or audible) or data, including similar functional devices not yet invented, may be used. The kiosk 102 may further support a server 104 or a printer 164, or other apparatus including software applications that may be added or used to upgrade the dispensing capability of the system. One item that may be included in the arrangement of equipment supported in the kiosk 102 is an auxiliary database 116 as shown in FIG. 6 herein above. An auxiliary database 116 may be used to store data particular to one automated dispensing machine or one group of machines among a plurality of dispensing machine groups in a health care facility, in order to realize operating efficiencies or other operational improvements to the system.

Continuing with FIG. 8, an automated prescription drug dispensing machine (ADM) 100 is illustrated in simplified form with its cabinet door opened to reveal banks 170 of dispensing canisters 172 therein. The canisters may be as described in FIGS. 3 and 4. After canisters 172 are loaded with the medication and are ready for dispensing, they may be plugged into one of the canister banks 170 in any open position. Mechanisms (not shown) within the ADM 100 cabinet provide for dispensing a unit of medication into a package prior to ejection from the machine. An ejection port 178 is provided in a convenient location on the dispensing machine 100. The ejection port 178 includes an opening from which a strip of medication packages 180 is fed under machine control. The strips of transparent packages may include a printed label 182 and may be separated by crosswise perforations 184 to enable separating the packages prior to administration to a resident.

FIG. 9A illustrates a first portion of a flow chart 200 for the basic operation to provide for ordering and dispensing a prescription drug in a long term care facility by the system whose architecture is illustrated in FIG. 7. The steps will include references to the unit of the system, as shown in FIGS. 6 and 7, that is active or where the step is carried out. The process begins at step 202 in which, both monthly and for any new resident being admitted, the resident is entered into the electronic health record (EHR) 126 and information regarding Medicare part D or Medicaid is verified and updated as necessary. This step may be carried out in the long term care (LTC) facility 94. In the following step 204, any new order for a prescription medication is entered at the prescription order entry (POE) 120 unit, which may be located in the pharmacy 92, the LTC 94, or the office (not shown) of a health care provider. This step includes verifying third party payer (insurance or other health care benefit) coverage, checking for drug allergies of the resident and possible drug interactions with other prescriptions the resident requires, and verifying that the new prescription is approved for dispensing at the order dispensing system (ODS) 98 on site at the LTC resident's location. The flow then advances to step 206 to transmit the prescription order to the pharmacy 92 and to enter the information into the EHR 126 for the resident at the LTC 94. The EHR 126 may be located typically in the main database 114 at the hosting center 84 or the auxiliary database 116 associated with the order dispensing system 98 at the LTC 94.

Continuing with FIG. 9A at step 208 the pharmacy 92 receives and reviews the order, then initiates formulary management processing to determine whether the prescription requires a brand name (coded "B") or branded generic (coded "BG") medication or a generic product (coded "G") may be substituted for the prescribed drug. Subsequently the order is submitted to the order dispensing system (ODS) 98 through the order management system (OMS) 90 to process the filling of packets preparatory to dispensing as will be described in FIG. 11 to follow. After step 208, the process advances to step 210 in which the OMS 90 notifies the prescription order entry (POE) 120 when the order has been approved by a pharmacist. Then, the order data is stored in the main database 114, and the OMS 90 determines the destination LTC 94 and the order dispensing system 102 to receive the order, and the order is queued for dispensing at the designated ODS 98 in the LTC 94. At the ODS 98 in step 212 the order proceeds to step 216 for delivery to the ODS 98 and installation into the automated dispensing machine 100 for dispensing and administering at the next scheduled time. The ODS 98 stores all of the identification and script data at the kiosk 102, then notifies the POE 120 that the order is queued for dispensing. Step 216 just described proceeds to step 222 along the path "A" in FIG. 9A, to FIG. 9B to be described next.

FIG. 9B illustrates a second portion of the flow chart for the basic operation of the system of FIGS. 6 and 7. Dispensing of medications occurs according to a predetermined schedule within the daily routine of the long term care or other health care facility. In the illustrated example the operation of the dispensing process may be initiated and controlled from the workstation 104 at the kiosk 102 associated with the dispensing machine 100 that will be utilized. The dispensing and administering of the medications may generally be carried out by a medical aide or assistant under the supervision of the director of nursing 96 or other registered nurse at the LTC 94. In step 222 the system awaits entry of a request from the ODS 98, sent by the electronic Medical Administration Record or eMAR 104 that the schedule calls for dispensing and administering of medications at a scheduled time. Accordingly, in step 224 the medical aide or assistant will operate the automated dispensing machine (ADM) 100 to package and dispense one or more packages of medications to be administered at a scheduled time as described further in FIG. 12. Typically, the ADM 100 will package a plurality of doses into a strip of separate packages separated by perforations. The doses in each successive package may then be administered to one resident after another who reside in close proximity, for example. Each administering of a dose is then recorded in the eMAR 104 by the medical aide or assistant before proceeding with the next dose. This action includes, step 226, notifying the OMS 90 that the administering of the prescribed dose has been completed and the record in the database 116 may be updated as depicted in step 228. At the conclusion of this process the OMS 90 notifies the pharmacy information system (PhIS) 124 in step 230 that the billing process may be carried out, after which the process ends in step 232.

Figure 10:
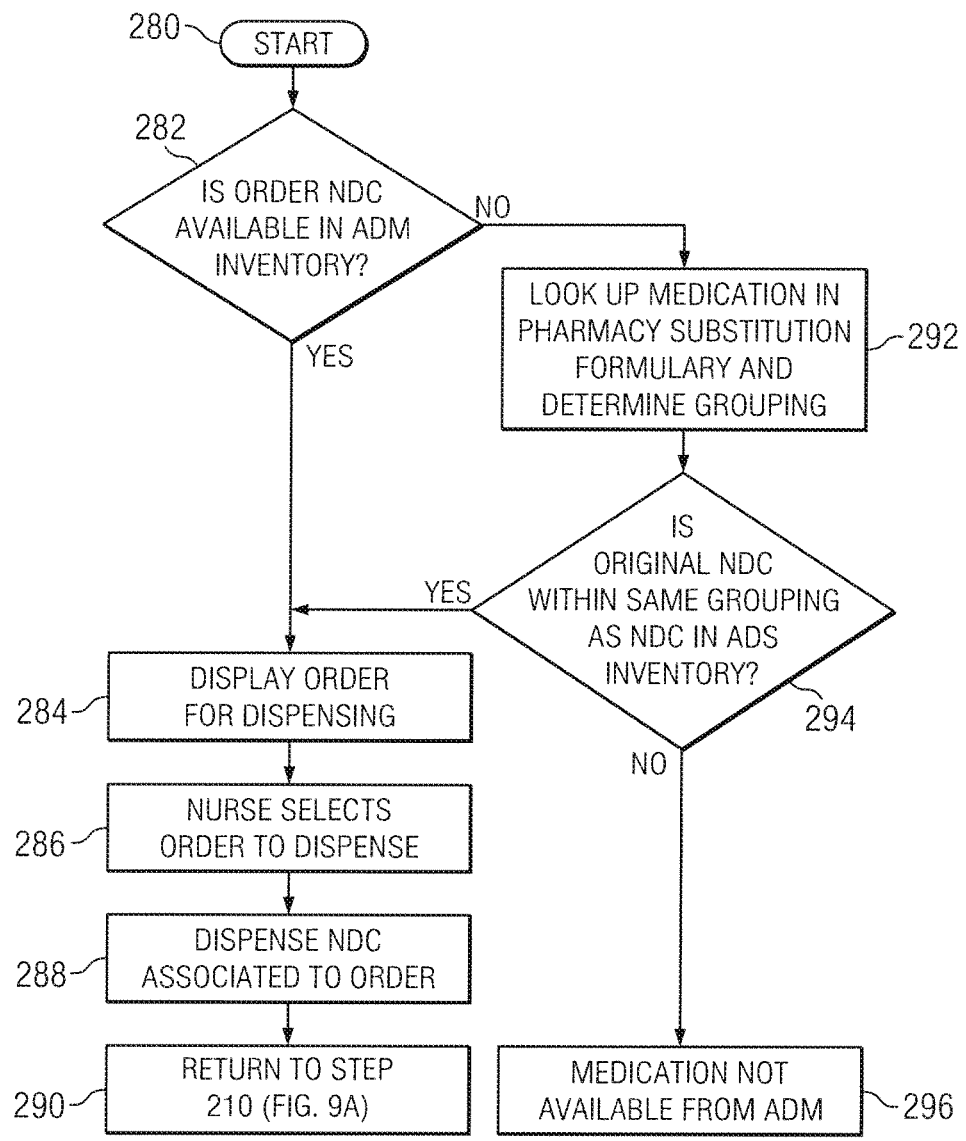
FIG. 10 illustrates a flow chart of one embodiment of a process 280 for formulary substitution as disclosed herein.

FIG. 10 illustrates a flow chart of one embodiment of a process 280 for formulary substitution according to the present invention. It is described elsewhere that configuring the canisters 50 at the pharmacy 92 and utilizing a compact set of ID data in the canister memory chip 60 provide very substantial improvements in operating and processing speed, efficiency, and error reduction in the prescribing and dispensing of prescription medications in resident health care facilities. One of the exemplary enhancements is the ability to manipulate formularies and reconfigure the canisters accordingly, a capability that does not exist when the canisters are configured by the canister manufacturer. All that the manufacturer can do is manufacture canisters for every type of medication, including the wide variety of formularies that are available. In the present invention, in which the canisters can be configured by the pharmacy, the canisters can be configured on the spot for a particular formulary that is suitable to be dispensed to a resident, even when the pharmacy must respond in real time circumstances. FIG. 10 illustrates a process by which this may be accomplished in the system of the present invention.

The process for FIG. 10 begins at step 282 after advancing from step 208 (see FIG. 9A) to perform the sub-process of formulary substitution, a subset of formulary management illustrated herein in the exemplary system. Recall that prescription medications are classified as branded, branded generic, or generic, depending on what source of manufacture may be accepted for administering to the resident. Thus, the process opens in step 282 by determining the formulary requirement of the "script" and responding to the query "Is order NDC available in the ADM inventory?" In other words, is this NDC stocked in the ADM 100? The script is a statement specifying the requisite formulary, the amount of the dose, how often and when the dose is to be administered. If the response in step 284 is YES, the script permits a substitution of "B," "BG," or "G," then a list of the medications available having the same status or classification will be displayed on the display of the workstation 160 at the kiosk 102 to enable a selection to be made by the nurse in step 286 and entered into the record, followed by step 288 to dispense the order. The ODS receiving the order advances to step 290 to return to step 210 in FIG. 9A. Returning to step 282, if the NDC ordered is not available in the ADM 100 inventory, the flow goes to step 292 to look up the medication in a pharmacy substitution formulary and determine the appropriate grouping, B, BG, or G. Then, in the query step 294, if the original NDC is within the same grouping as the NDC in the ADM 100 inventory (a YES response), the flow advances to step 284 and proceeds as described previously. If, in step 294, the NDCs do not match because the formulary medication is not available in the ADM 100, then the process goes to step 296 to exit, and the process ends.

The automated dispensing machine (ADM) 100 as described previously is an automated machine for packaging and dispensing prescription medications under computer control. Medications for a supply of doses to be stored in the machine are deposited in individual canisters 50 as described in FIGS. 3 and 4 herein. A typical ADM 100 may contain approximately 200 canisters, for example. The actual number depends on the volume of the main body of the canisters, which may vary depending on the size and form of the individual does to be contained in the canister 50. The supply quantity of medications for an individual canister 50 may be determined by the needs for some interval of time, e.g., one month, or by the needs for one or more residents in the LTC 94. The processes for configuring, filling, and changing the contents of the canisters is illustrated in FIGS. 11A through 11F.

Figure 11A:
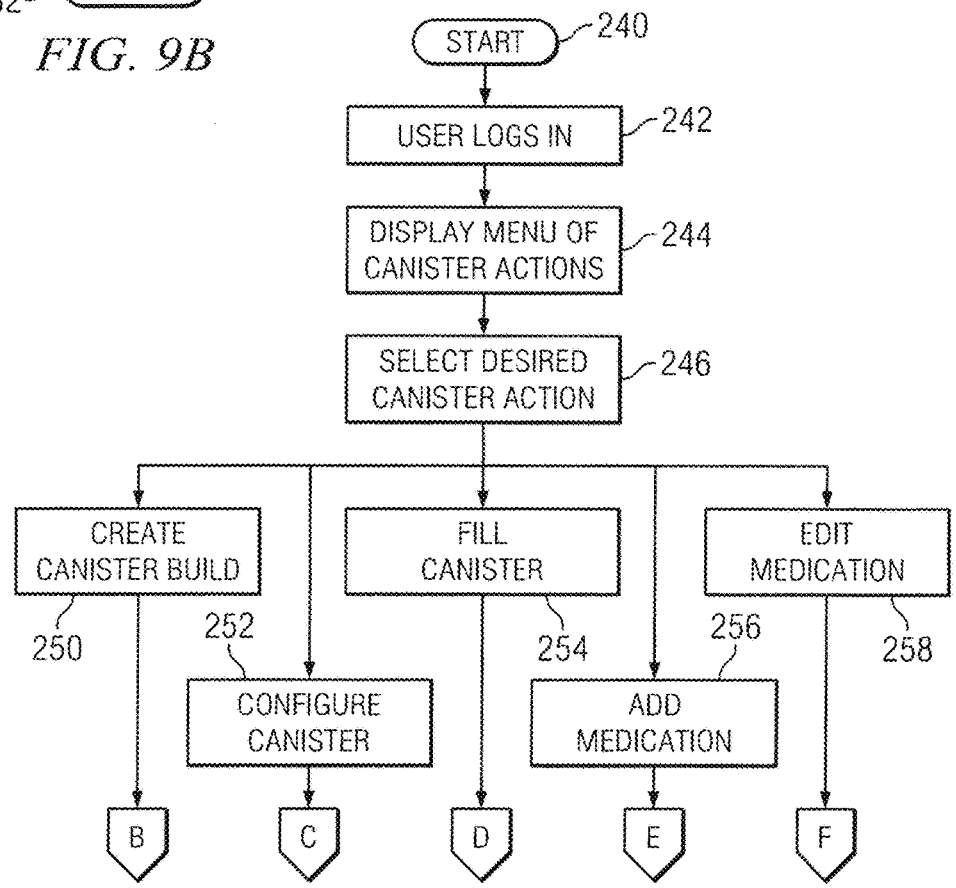
FIG. 11A illustrates a flow chart of initial steps to begin a medication canister configuration and fill process according to at least one embodiment as disclosed herein.

FIG. 11A illustrates a flow chart 240 of initial steps to begin a medication canister configuration and fill process according to one embodiment of the present invention. The flow begins at user log in at step 242 and the display of a menu of actions that involve the configuration, filling, or modifying the fill or information affecting the canisters in step 244. In step 246 the user may select the desired action from the menu, which lists five different actions, respectively: create canister build; configure canister; fill canister; add medication to the canister; and edit the medication information of the canister. These actions are respectively designated as steps 250, 252, 254, 256, and 258. Selecting any one of these options directs the user along respective paths B through F of FIG. 11A to corresponding processes illustrated in FIGS. 11B through 11F to be described herein below.

Figure 11B:
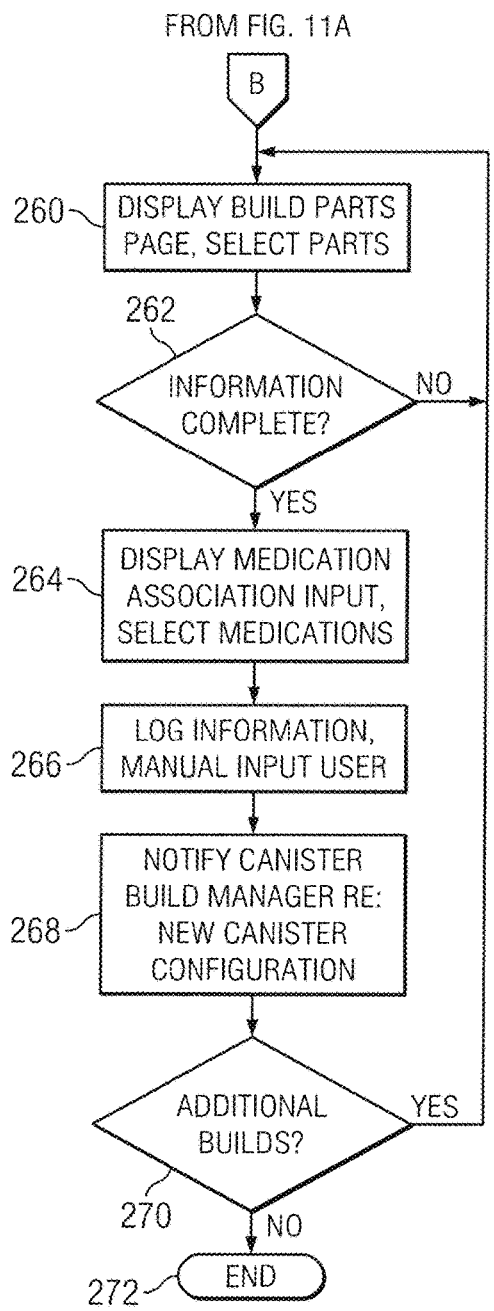
FIG. 11B illustrates a flow chart of a process to create a canister build as disclosed herein.

FIG. 11B illustrates a flow chart of a process to create a canister build according to the present invention. A canister build is the process for configuring a canister for a specified medication. As described in FIGS. 3 and 4, the configuration of a canister may be adapted to the quantity, size, and shape of the individual doses of the medication to be stored or contained therein. The flow enters step 260 from path B, displays build parts on a displayed page, and enables selection of build parts appropriate to the prescription order being fulfilled. Following the selection of parts, a query step 262 as to whether the needed information is complete provides a YES alternative to step 264 to display a medication association input and select the medication that is to be deposited into the canister. Step 262 also provides a NO alternative to return to step 260 if the information is not complete. Following the selection of medication(s) for deposit into the canister in step 264, the process advances to step 266 to log the information about the canister and provide for the user's manual input of information about the canister build. In the following step 268, the canister build manager is notified of the new canister configuration in step 268. Next, if there are any additional canister builds to process, as queried in step 270, the flow returns to step 260; if not, the flow ends at step 272.

Figure 11C:
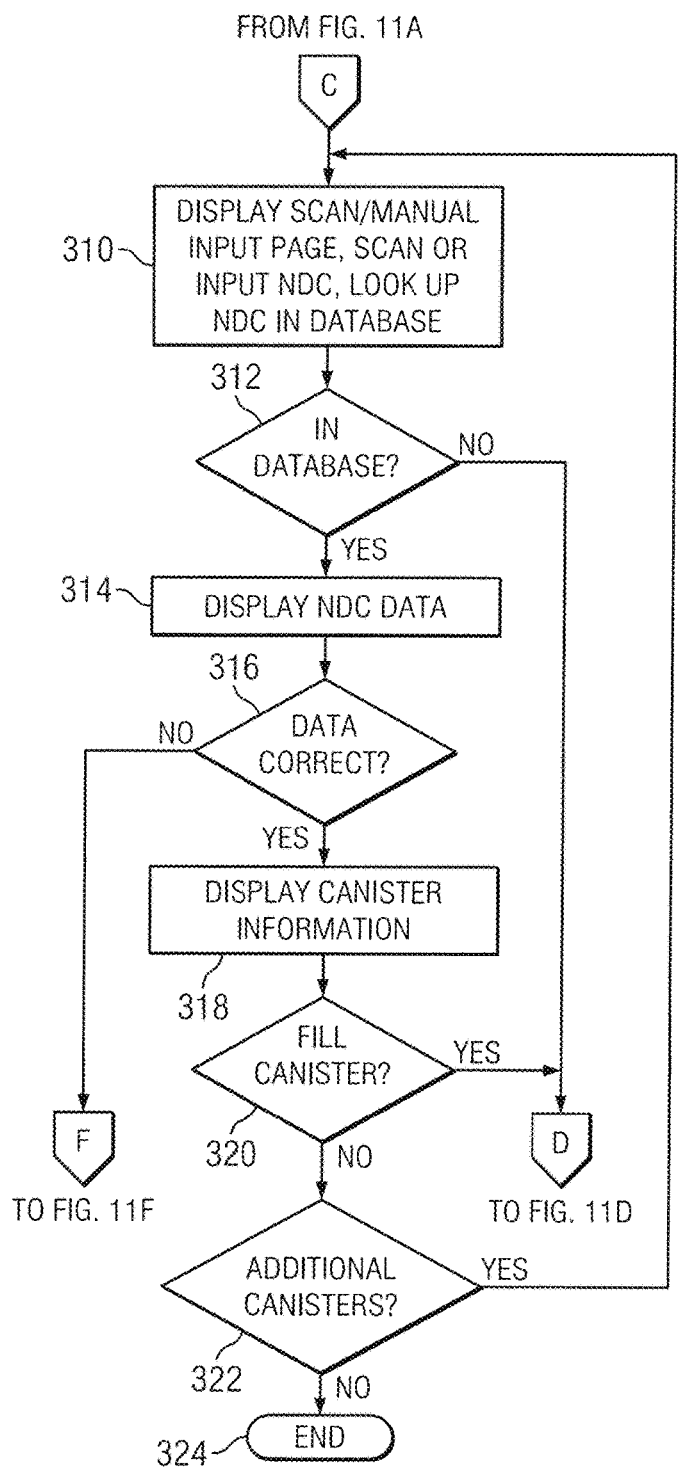
FIG. 11C illustrates a flow chart of a process to configure a canister as disclosed herein.

FIG. 11C illustrates a flow chart of a process to configure a canister according to the present invention. The flow enters step 310 from path C, displays a scan/manual input page to enable the user to enter or scan the NDC for the prescription medication, and look up the NDC information in the main database 114 or, in some cases, the auxiliary database 116 as shown in FIG. 7. If the information sought is in the database (YES, in step 312), it is displayed in step 314, followed by a check query "Data Correct?" in step 316, and if YES to that query, advances to step 318 to display the canister information. If the canister is to be filled with the designated quantity, the YES response to the query in step 320 is entered and the process exits to path D to be described in FIG. 11D. Returning to step 312, if the response to the query "Is the NDC data in the database?" is NO, the process also exits to path D. Further, in step 316, if the response to the query "Is the data correct?" is NO, then the flow exits to path F to be described in FIG. 11F. Returning now to step 320, if the response to the query "Fill canister?" is NO, then the flow proceeds to step 322, a query as to whether any additional canisters are to be filled. If YES, the flow returns to step 310; if NO, the process ends at step 324.

Figure 11D:
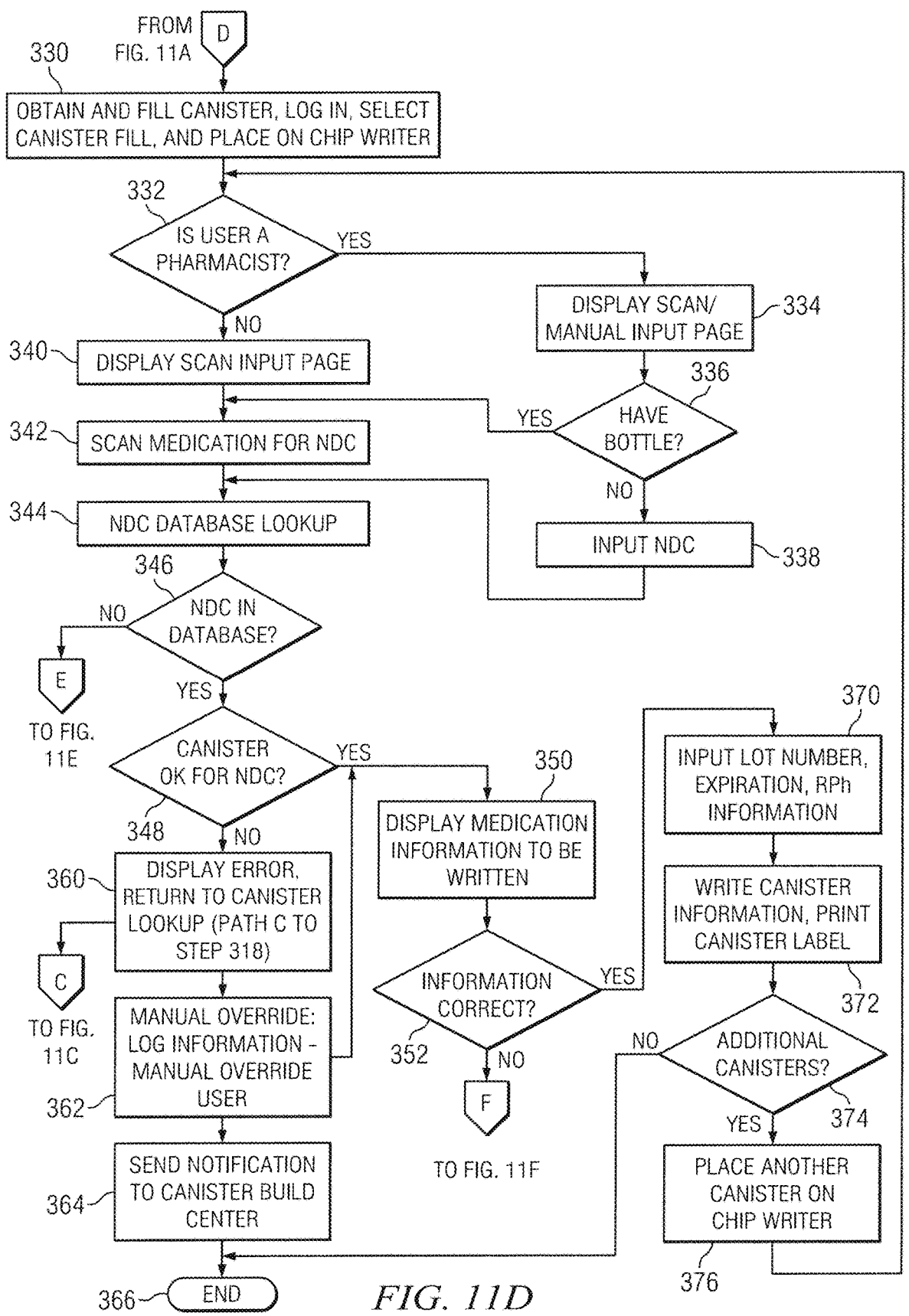
FIG. 11D illustrates a flow chart of a process to fill a canister as disclosed herein.

FIG. 11D illustrates a flow chart of a process to fill a canister according to the present invention. Canisters are generally filled at a pharmacy 92 that stocks the medications and is under the supervision of a registered pharmacist as required by law. The present invention includes the ability to configure the canisters 50 at the pharmacy 92, at the time the canister is to be filled. In conventional systems the configuration of the canisters is accomplished to order by the canister manufacturer before shipment to the pharmacy operator. The pharmacy must stock all of the different configurations of the canisters that it needs to fulfill orders for the prescription medications from the long term or other health care facilities that it services. Because of the very wide variety of formularies, forms, shapes and sizes of the medications, the pharmacy must maintain an extensive and expensive inventory of configured canisters. The present invention overcomes this problem by stocking the interchangeable component parts of the canisters—a much smaller number of SKUs (stock keeping units). The efficiencies gained from this technique are substantial because each canister can be configured as needed, thus avoiding the inventory of configured canisters not being used. Further, canisters can be readily modified from one configuration to another with minimal effort, thus minimizing the likelihood that a dispenser is out of service because a particular canister is not available. Moreover, quality control, inspection, repair and maintenance operations are significantly more efficient and less likely to cause delays because all of these operations can take place at the pharmacy where the canisters are configured or filled.

Continuing with FIG. 11D, the flow begins on path D to step 330 to obtain and fill a canister, the user logs in to the system, selects "canister fill" on the workstation screen, and places the canister 50 on a chip writer (not shown). As shown in FIGS. 3 and 4, the canister memory chip extends slightly below the underside of the canister 50, enabling it to be inserted into a receptacle on the chip writer for writing the data thereto. In the next step, the system queries the user to ascertain whether the user is a registered pharmacist. If YES, the process advances to step 334 to display the scan/manual input page, wherein the user may select which of these modes—scan or input manually—will be used. If scan is selected a scanning device such as (but not limited to) a bar code scanner may be used. In the next step 336 the system determines whether the user has a bottle of the medication to be utilized, and if YES, the flow goes on to step 342. If, however, the user does not have a bottle, the flow advances to step 338 to scan or input the NDC, the Nation Drug Code, to the system, followed by the step to look up the NDC in the database 114. Returning to step 332, if the user is not a pharmacist, the system displays the scan input page on the screen of the workstation in step 340 before advancing to step 342 to scan the medication for its NDC.

Figure 11E:
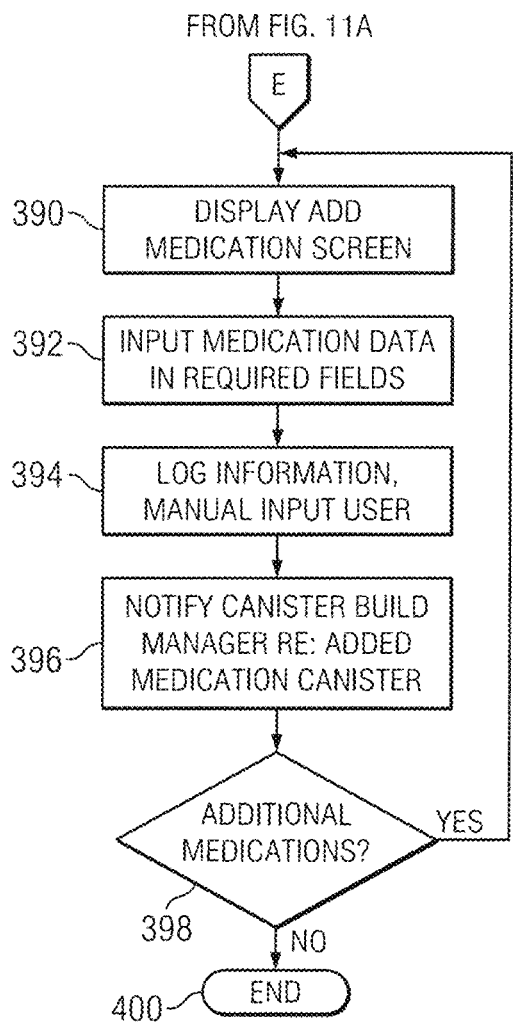
FIG. 11E illustrates a flow chart of a process to add a medication canister as disclosed herein.

Following step 344, the system determines whether the NDC is found in the database 116? If NO, the process exits along path E to FIG. 11E. If YES, the process steps to step 348 to determine whether the canister is OK for NDC, that is, whether its configuration matches or is compatible with the drug attribute information for the particular pill, capsule, tablet, etc. If YES, then the flow advances to step 350 to display the medication information to be written into the database and the build ID and Canister/Fill Ids written onto the canister memory chip. If this information is NOT correct, then the process at step 352 exits along path F to FIG. 11F to edit the information. Returning to step 352 if the information is correct, the process proceeds to step 370 in which the Lot Number, expiration information, and the registered pharmacist information is input to the system, followed in step 372 by writing the canister information and printing the canister label. Next, the flow advances to determine whether additional canisters need to be filled in step 374 and if the response is NO, the process ends at step 366. If the response is YES, the process prepares to place another canister on the canister chip writer in step 376 and then flows back to step 332 to re-enter the fill processing procedure.

Returning to step 348, if the canister is determined to NOT be suitable for the NDC that the user wishes to deposit in the canister, then the flow proceeds to step 360 wherein the system displays the error. The user has an option to return to the "Canister Lookup" step 318 in FIG. 11C or select a manual override as in step 362. If the "manual override" is selected at 362, the system will send a notification of the error and the manual override to the canister build center in step 364 before ending the routine in step 366.

FIG. 11E illustrates a flow chart of a process to add a medication canister according to the present invention. Entry to the process proceeded along path E following selection in step 246 of the action to "Add Medication" at step 256. At step 390 the display screen for adding a medication appears on the workstation display, enabling the user to input the medication data in step 392 in the respective fields for the medication to be added. This information may include for example a mnemonic, the NDC, the name of the drug, its strength, unit, manufacturer, color, shape, marking, and schedule for administering. The added information is logged and the user input manually in step 394, followed by step 396 to notify the canister build manager regarding the added medication. Next, in step 398 a query occurs whether there are any other additional medications to input. If YES, the flow returns to step 390 and the process repeats; if NO, the process ends.

Figure 11F:
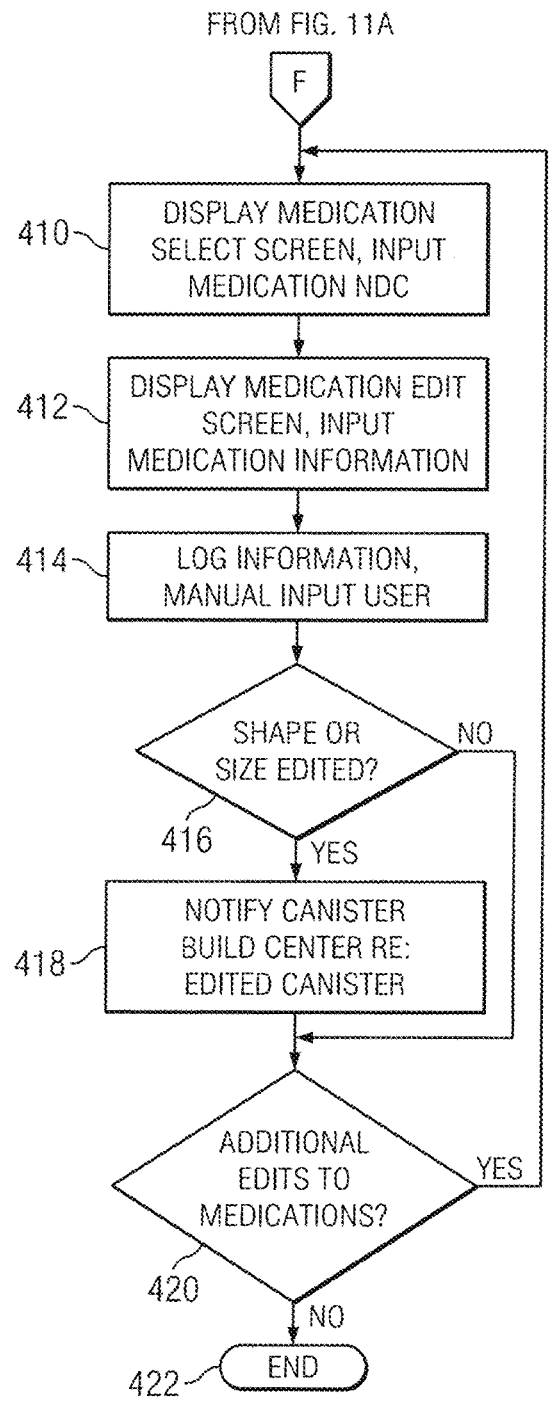
FIG. 11F illustrates a flow chart of a process to edit a medication canister as disclosed herein.

FIG. 11F illustrates a flow chart of a process to edit a medication canister according to the present invention. It is similar to the process for adding a medication and proceeds as follows. Entry to the process proceeded along path F following selection in step 246 of the action to "Edit Medication" at step 258. At step 410 the display screen for editing a medication appears on the workstation display, enabling the user to input the medication data in step 412 in the respective fields for the medication to be added. This information may include for example a mnemonic, the NDC, the name of the drug, its strength, unit, manufacturer, color, shape, marking, and schedule for administering. The edited information is logged and the user input manually in step 394, followed by a query step 416 whether the size or shape of the medication unit is to be edited. If YES, the flow proceeds to step 418 to notify the canister build center regarding the edited canister; if NO, the flow advances ahead of step 418 to another query step 420 whether there are any additional medications. If YES, the process returns to the step 410 to repeat the edit routine. If NO, the process ends.

Figure 12:
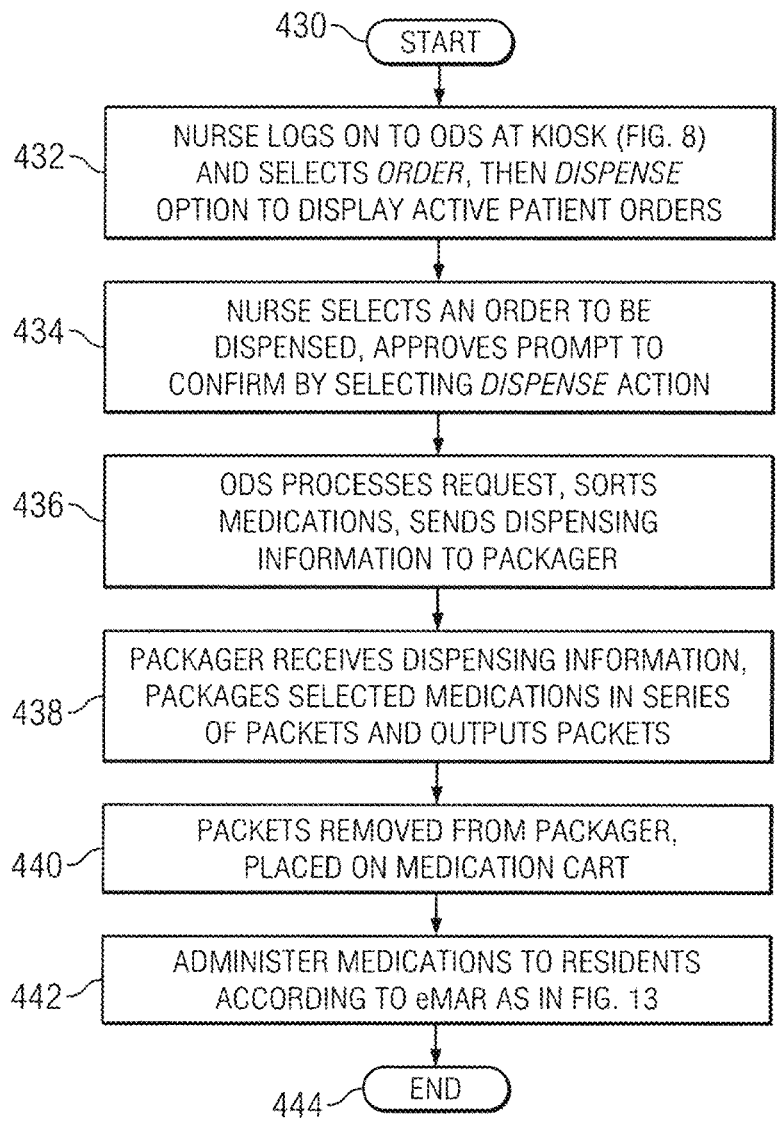
FIG. 12 illustrates a flow chart of a process to prepare medications for administering them to residents of a long term care facility as disclosed herein.

FIG. 12 illustrates a flow chart of a process 430 to prepare medications for administering them to residents of a long term care facility according to the present invention. The first step 432 occurs as the nurse logs on to the order dispensing system (ODS) 98 at the kiosk 104 (See FIG. 8) and selects Order, then the Dispense option displayed on the workstation screen of the kiosk 104 to display active patient or resident orders. Then in step 434 the nurse selects an order to be dispensed, approves a prompt to confirm by selecting the Dispense option. Next, in step 436 the ODS 98 processes the request, sorts the medications, sends dispensing information to the packager in the automated dispensing machine (ADM) 100. Upon receiving the dispensing information the packager, in step 438 packages selected medications in a series of individual packets delineated by cross-ways perforations to facilitate ease of tear-off separation, and outputs the packets from the port 178 on the ADM 100. The nurse or assistant may then remove the strip of packets from the ADM 100 in step 440 and place the strip 180 on a medication cart (not shown) for delivery to residents scheduled to receive the medications in the strip 180 of packets. In the last step 442 the medications are administered to residents according to the eMAR as will be depicted in FIG. 13 to follow.

Figure 13:
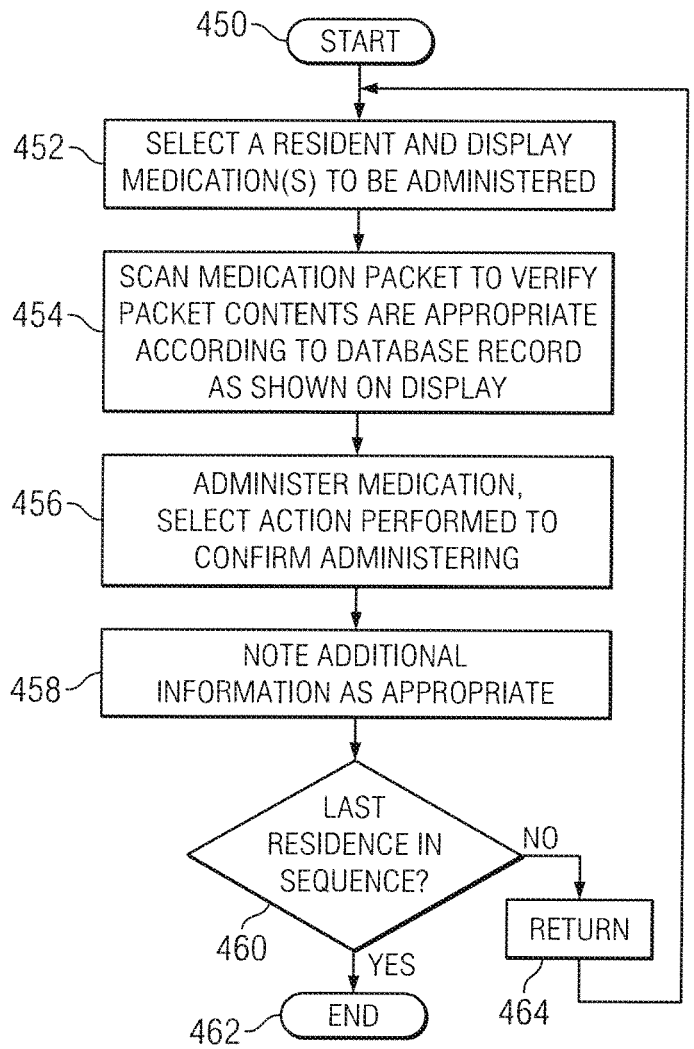
FIG. 13 illustrates a flow chart of a process for administering medications to residents of a long term care facility as disclosed herein.

FIG. 13 illustrates a flow chart of a process 450 for administering medications to residents of a long term care facility according to the present invention. The process begins at step 452 in which an assistant selects a resident on a display of a workstation to display the medication(s) to be administered. Next, in step 454 the assistant scans the medication packet to verify the packet contents are appropriate according to the database record as shown on the display. Then the flow proceeds to step 456 to administer the medication, select the action performed to confirm the administering of the medication. The process continues at step 458 with an opportunity to record additional information as appropriate, and concludes with a query step 460 whether the medication last administered is the last resident in the scheduled sequence? If the result is YES, the process ends; if the result is NO, the process returns via step 464 to the beginning of the process 450 at step 452.

Figure 14:
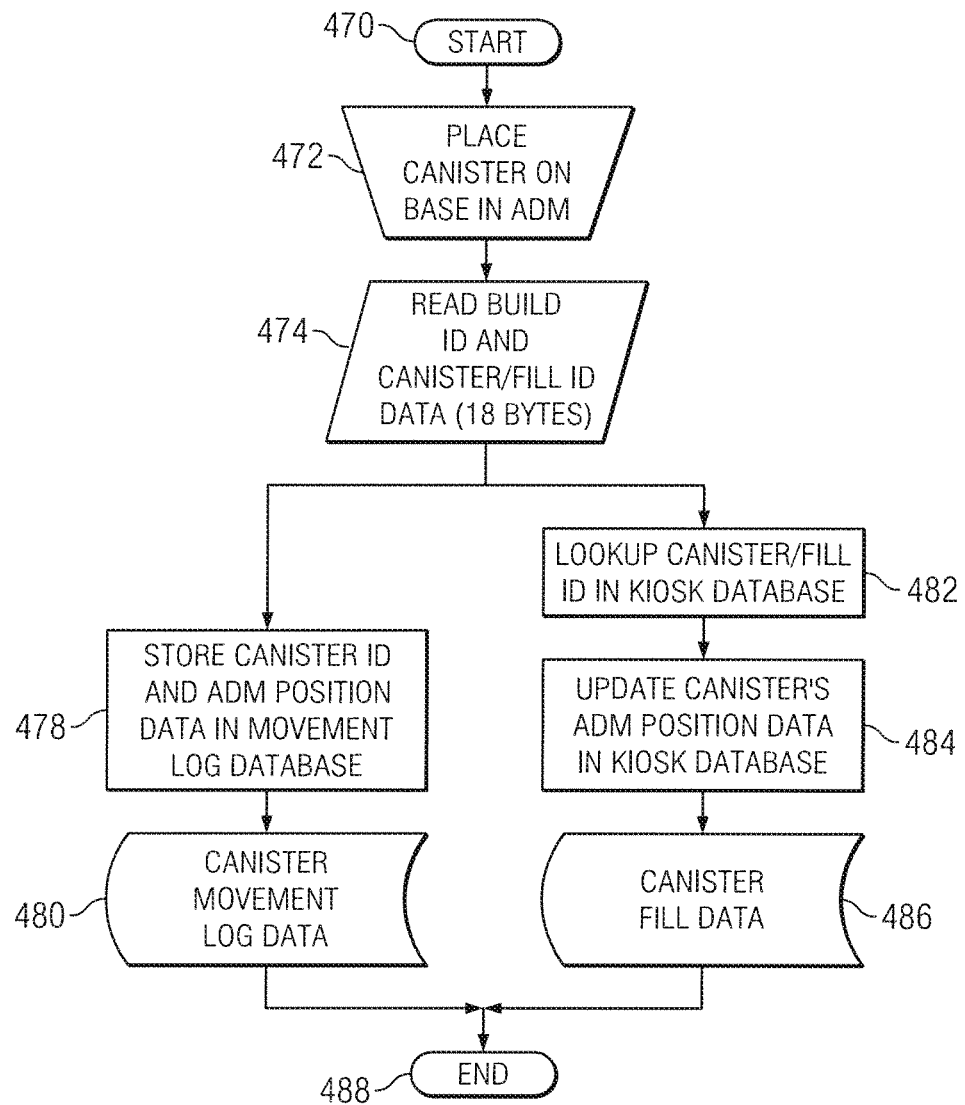
FIG. 14 illustrates a simplified flow diagram for reading medication data from a canister memory as disclosed herein.

FIG. 14 illustrates a simplified flow diagram 470 for reading medication data from a canister memory 60 according to the present invention to highlight the reduction in processing and dispensing time, and errors in dispensing afforded by the modified memory contents. Beginning at step 472, the canister 50 is placed on a base in the ADM 98 that contains a keyed receptacle (not shown) that matches the guide block 80 (See FIG. 4) on the underside of the canister 50. In step 474 the Build ID and Canister/Fill ID data (18 bytes total) are read. At this point the process follows two parallel paths simultaneously. Before proceeding, some terms need to be defined. A "canister movement log" contains data about the canister 50 that tracks the historical position of the canister 50 in the Automated Dispensing Machine (ADM) 100. "Canister movement data" represents the contents of the database where the movement data is stored. "Canister/fill data" represents the contents of the database where the canister/fill data is stored. "Fill data" is the data associated with the Fill ID of the canister.

Continuing with FIG. 14, advancing from step 474 proceeds along two parallel paths. In a first path, the flow advances to step 478 to store the canister ID and ADM 100 position data (the location in the ADM of the canister) in the movement log database. Step 480 represents the stored movement log data in the auxiliary database, which may reside in the server 104 or the workstation 160 at the kiosk 102, and the process ends at step 488. In the second path following step 474, the canister/fill ID is looked up at step 482 in the kiosk database, which is synonymous with the auxiliary database 116 in FIG. 6. Then the canister position data representing the canister's position in the ADM 100 is updated in the kiosk or auxiliary database 116. Step 486 represents the updated canister/fill data in the auxiliary database 116, and the process ends at step 488.

While the invention has been shown in only several of its forms, it is not thus limited but is susceptible to various changes and modifications without departing from the spirit thereof.

What is claimed is:

1. A canister of a medication dispensing system, the canister comprising:
a main body for housing and releasing medication comprising a plurality of individually provided medication;
an electronic memory containing a first canister code for identifying the canister,
wherein the electronic memory is configured to provide the first canister code to a remote database configured to retrieve, based on the first canister code, a second canister code for identifying a type of the medication contained in the main body, the remote database further configured to provide the second canister code to an automated drug packaging and dispensing machine containing the canister, and
the canister configured to be retained in the automated drug packaging and dispensing machine during operation and to release individually at least a portion of the plurality of individually provided medication contained therein, the releasing in response to the automated drug packaging and dispensing machine operating to release medication identified by the second canister code.

2. The canister of claim 1, wherein the electronic memory is configured to be operable with circuitry of the automated drug packaging and dispensing machine to operate with the automated drug packaging and dispensing machine and provide to the automated drug packaging and dispensing machine the first canister code for identifying the canister.

3. The canister of claim 1, further comprising a first label thereon, the first label containing specifications of the medication contained therein.

4. The canister of claim 3, further comprising the second canister code provided on at least one of the first label and a second label.

5. The canister of claim 1, wherein the main body comprises at least one interchangeable part configured to be exchanged for a different interchangeable part to accommodate a different type of medication being stored in the main body.

6. The canister of claim 5, wherein the remote database comprises a record associating (i) the first canister code for identifying the canister with (ii) the second canister code for identifying the type of the medication contained in the main body, and
wherein the second canister code in the remote database is configured to be modified in the remote database to identify the different type of medication being stored in the main body.

7. The canister of claim 1, wherein the plurality of individually provided medication is in a form of a pill, tablet, caplet, or capsule.

8. The canister of claim 1, wherein the type is based in part on dimensional attributes of the medication.

9. The canister of claim 1, wherein the main body comprises at least one adjustable part configured to be adjusted to accommodate a different type of medication being stored in the main body.

10. A method for providing a first configurable canister with a first memory device thereon, the method comprising:
storing a first data set in a database (i) separate from the first memory device and (ii) not in the first memory device, the first data set comprising at least a code identifying at least a first medication to be stored in the first configurable canister for dispensing by an automated dispensing machine in communication with the database;

storing a second data set in the database (i) separate from the first memory device and (ii) not in the first memory device, the second data set comprising a code corresponding to a structural configuration of the first configurable canister, the structural configuration of the first configurable canister comprising a first structural configuration, the first structural configuration corresponding to attributes of the first medication to be stored in the first configurable canister for dispensing by the automated dispensing machine;

assembling the first configurable canister in accordance with the first structural configuration, wherein at least a type of medication in the first data set is associated with the first structural configuration in the second data set and the association is stored in the database (i) separate from the first memory device and (ii) not in the first memory device;

reading, from the first memory device of the first configurable canister, data representing a canister ID stored thereon;

storing, in the database (i) separate from the first memory device and (ii) not in the first memory device, the canister ID that was read from the first memory device of the first configurable canister;

electronically associating, in the database (i) separate from the first memory device and (ii) not in the first memory device, (a) the canister ID, (b) the first structural configuration, and (c) the type of medication;

storing the association in the database (i) separate from the first memory device and (ii) not in the first memory device;

providing the canister ID from the first memory device of the first configurable canister, wherein the canister ID is configured to be read from the first memory device of the first configurable canister by the automated dispensing machine that is in communication with the database, and wherein the automated dispensing machine is configured to retrieve the type of the first medication from the database in response to the reading the canister ID.

11. The method of claim 10, wherein the first structural configuration in the second data set is represented by a code.

12. The method of claim 11, wherein the code is a four digit code.

13. The method of claim 10, wherein the database is a distributed database.

14. The method of claim 10, further comprising incrementing a counter stored on the first memory device, a value of the counter corresponding to a number of times the first configurable canister has been filled.

15. The method of claim 10, wherein the attributes of the first medication are selected from one or more of a form of the first medication, a size of the first medication, and a shape of the first medication.

16. The method of claim 10, wherein the first configurable canister is configured to be filled with only medication having only attributes associated with the first structural configuration of the first configurable canister.

17. The method of claim 10,
wherein the first configurable canister may be reconfigured to a second structural configuration associated with a second medication having different attributes than the first medication, and wherein the method further comprises replacing the first structural configuration in the second data set with the second structural configuration.

18. The method of claim 10, wherein assembling the first configurable canister in accordance with the first structural configuration comprising adjusting the first configurable canister.

19. A configurable canister management system comprising:

a configurable canister comprising a memory device,
wherein the memory device is configured to communicate with a database,
wherein the memory device stores a canister ID comprising (i) data identifying the configurable canister, and (ii) data corresponding to a counter of a number of times that the configurable canister has been attached to a filling station and filled with a medication,
wherein the filling station includes a computer in operative communication with the database, and
wherein the database stores data identifying a structural configuration of the configurable canister and associates the structural configuration with (i) the medication and (ii) the canister ID.

20. The configurable canister management system of claim 19, wherein the memory device comprises a memory control circuit configured to provide the canister ID to an automated medication dispensing machine to which the configurable canister is connected following disconnection from the filling station.

21. The configurable canister management system of claim 19, wherein the database is a distributed database.

22. The configurable canister management system of claim 19, wherein the configurable canister further comprises a label identifying one or more of the medication and the canister ID.

23. The configurable canister of claim 19, wherein the configurable canister further comprises a label providing at least a portion of the data identifying the structural configuration associated with the configurable canister.

24. A method of filling a configurable canister with a medication, the method comprising:

connecting a configurable canister to a filling station, wherein the configurable canister comprises:
a main body for housing and releasing medication comprising a plurality of individually provided medication in a form of a pill, tablet, caplet, or capsule; and
an electronic memory connectable to the filling station and containing (i) a first canister code for identifying the configurable canister, and (ii) a fill counter for tracking a number of times the configurable canister is filled with medication;

reading, by the filling station, the first canister code;

writing, to a database, an update to a record associated with the first canister code, the update comprising data corresponding to an NDC code of a medication for filling into the configurable canister;

incrementing, in the electronic memory, a value of the fill counter;

disconnecting the configurable canister from the filling station and connecting the configurable canister to an automated dispensing machine;

reading, by the automated dispensing machine, the first canister code from the configurable canister;

providing, by the automated dispensing machine, the first canister code to the database; and retrieving, by the automated dispensing machine and from the database, the record associated with the first canister code, the record comprising the NDC code of the medication in the configurable canister.

25. The method of claim 24, further comprising:
prior to the writing to the database the update, (i) providing, by the filling station, the first canister code to the database, and (ii) retrieving, by the filling station and from the database, the record associated with the first canister code that was transmitted to the database.

26. A method of configuring a configurable canister to dispense a medication, the method comprising:
providing, to a database and by a filling station, an NDC code of a medication for filling into a configurable canister;
retrieving from the database and at least partially in response to the providing, at least one build ID corresponding to at least a first configurable canister configuration indicated by the database to be compatible with attributes of the medication associated with the NDC code;
retrieving a set of one or more out-of-service canister IDs, each canister ID of the set of one or more out-of-service canister IDs comprising a unique identifier associated with an out-of-service configurable canister that (i) is presently out-of-service and (ii) has a build ID that corresponds to the presently out-of-service configurable canister that is available for use with the filling station;
in response to the retrieving, determining that no available out-of-service configurable canisters associated with the set of one or more out-of-service canister IDs has the build ID corresponding to at least the first configurable canister configuration that is compatible with the attributes of the medication associated with the NDC code;
in response to the determining, retrieving a parts list associated with the at least one build ID corresponding to at least the first configurable canister configuration compatible with the attributes of the medication associated with the NDC code;
providing data to the filling station corresponding to human-readable instructions for changing at least one part of at least one available out-of-service configurable canister associated with the set of one or more out-of-service canister IDs, in response to the parts list, and to cause the at least one available out-of-service configurable canister associated with the set of one or more out-of-service canister IDs to have a new build ID corresponding to compatibility with the attributes of the medication associated with the NDC code;
reading, by the filling station, the canister ID of the at least one out-of-service configurable canister having the new build ID;
providing, by the filling station, the canister ID of the at least one out-of-service configurable canister having the new build ID to the database; and
writing, by the database, the canister ID to a record associated with the new build ID to document that the at least one out-of-service configurable canister having the new build ID is now compatible with the attributes of the medication associated with the NDC code.

27. The method of configuring the configurable canister to dispense the medication according to claim 26, wherein the database includes a plurality of databases containing different information.

28. The method of configuring the configurable canister to dispense the medication according to claim 26, wherein the database comprises a distributed database.

* * * * *